US007771997B2

(12) United States Patent
Chen et al.

(10) Patent No.: US 7,771,997 B2
(45) Date of Patent: Aug. 10, 2010

(54) ENHANCED EXPRESSION AND STABILITY REGIONS

(75) Inventors: Gang Chen, Yorktown Heights, NY (US); Robert Babb, Nauet, NY (US); James P. Fandl, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 28 days.

(21) Appl. No.: 12/132,846

(22) Filed: Jun. 4, 2008

(65) Prior Publication Data

US 2009/0124005 A1 May 14, 2009

Related U.S. Application Data

(60) Provisional application No. 60/933,213, filed on Jun. 4, 2007.

(51) Int. Cl.
*C12N 5/10* (2006.01)

(52) U.S. Cl. ...................... 435/358; 435/69.1; 435/367

(58) Field of Classification Search ...................... None
See application file for complete search history.

(56) References Cited

U.S. PATENT DOCUMENTS 6,689,606 B2 * 2/2004 Antoniou et al. ............ 435/325

* cited by examiner

*Primary Examiner*—James S Ketter
(74) *Attorney, Agent, or Firm*—Kevin J. Pobursky; Tor E. Smeland, Esq.; Valeta Gregg, Esq.

(57) ABSTRACT

Expression-enhancing nucleotide sequences for expression in eukaryotic systems are provided that allow for enhanced and stable expression of recombinant proteins in eukaryotic cells. Enhanced expression and stability regions (EESYRs) are provided for expression of a gene of interest in a eukaryotic cell. Chromosomal loci, sequences, and vectors are provided for enhanced and stable expression of genes in eukaryotic cells.

8 Claims, 13 Drawing Sheets

Fig. 3A

```
EESYR              5032 TT--------------CCTGAGTTCCGCCAA-CGCCTAGTGACATCCTGTG----------  5067
Rat Ch3 trim       5008 TTTATC-----TTTCCCTGGGACAGCCAA-AGCCTGGTGGCATCCTCTGTGAAGTGTTC  5061
M Mus Ch2 trim     6021 TTTATC-----TTTCCCTGGGACCGCCAA-AGCCTGGTGGCATACTGTACATTCTG---  6071
H. Sap. Ch20 tr    5972 AGAAACACAACTTCTCCCAGGGAGAGTCAAGAGAGCAGTGTCATTTCCTATAAAATGTCC  6031
                                       **   *    * ***  *    *** ***    *

EESYR              5068 --------CACACCCT------AAGGTGGCCTTTGTGTGGC------ACTGGCTTGGGTG  5107
Rat Ch3 trim       5062 ATTCAAGACAGGCTCTGTCTTAAAGGTGGCCTTCGCATGGCGCTGGCACTGGCCGGGGCA  5121
M Mus Ch2 trim     6072 --------TACACTGTTCATTCAAAACAGGCTCTGTCTTAAA-----GATGGTCTGAGCG  6118
H. Sap. Ch20 tr    6032 A--AGGCCAATCCCAGGTCCCGGTGTCAGCCCTTGCGTGTGGC----ACTGGCACCAGCA  6085
                                 *  *               * *   *  *           ***     *

EESYR              5108 GTCGGGAAAGG-CATTTTCAGCTTGTT-GCAGAACTGCCACAGTAGCATGCTGGGT-CCG  5164
Rat Ch3 trim       5122 GTCAGGAGAGGGTATTTTTAGCTTCTTTGCAGAATGGCCTCAGGAGCGTGCTGAGT-CTG  5180
M Mus Ch2 trim     6119 GTCAGAAAAGGGTATTGTTAACTTGTTTGCAAAACTGCCTCAGGAGAGTGCTGAGT-GCG  6177
H. Sap. Ch20 tr    6086 GCCAGAAAGGT-TACTTGTGACTTGTTTTCAGTGCTTTCCTGGGAGTGTCCTGAAAGCTG  6144
                        * * * *  *   * *     *** **  **       *   * **  * ***      *

EESYR              5165 TGAAAGTTTCTGCCCGTTAACAAGAAGTCTCTACTACTTGTGACCTCACCA-----GTGA  5219
Rat Ch3 trim       5181 TGAAAGTTGCTGCCAGTTAAGGAGAAGTCTCTACCACTCGTGACCTCACCA-----TTGA  5235
M Mus Ch2 trim     6178 TGAAAGTTGCTGCCCGTTAAGGAGAAGTCTCTACTACTTGTGATCTCACCA-----TCGA  6232
H. Sap. Ch20 tr    6145 GCAGTGTTTCTGCCTCGTCAGAAGAGGCCTCATTCATTTGGGGTTGTACCAGCAACTTAA  6204
                          * *** *****   * *  *** * ***    * * * *     ****        *

EESYR              5220 AAATTTCTTTAATTG------TCTCCTGGTGTTC-TGGGTTTTG-------CATTTTTGT  5265
Rat Ch3 trim       5236 AAATTTCTTTAATTG------TCTCCTCGTGTTC-TGGGCTTTG-------CAGTTTTGT  5281
M Mus Ch2 trim     6233 AAATTTCTTTAATTG------TCTCCTGGTGTTC-TGGGTTTTG-------CAGTTTTGT  6278
H. Sap. Ch20 tr    6205 AAAGTTTTTTTTTTCTTCCCTCTTCCAGTGTTAATAGATTTTGAAAGAGGCATTTTTGT  6264
                        *** ** ***  **       *** *  *****  * *  ****       ** ******

EESYR              5266 TTCTAAGGATACATTCCTGGGTGATGTCATGAAGTCCCCAAAGACACAGTG-GGGCTGTG  5324
Rat Ch3 trim       5282 TCCTAAGGATACATTCTTGGGTGATGTCACGAAGTCCCCAAAGACACAGTG-GGGCTGTG  5340
M Mus Ch2 trim     6279 TTCTAAGGATACATTCTTGGGTGATGTCACAAAGTCCCCAAAGACACGGTG-GAGCTGTG  6337
H. Sap. Ch20 tr    6265 TTCTAATTACAAATTCCTGGGTGATGTCATTAAGCCCTCAAACACCCGGTGAGGGCGGCA  6324
                        * ****  * * **** ************  *** ** **** ** * *** * ** *

EESYR              5325 TTGGATTGGGAAAGAT------------GATTTATCTGG-GGTGTCAAAAGGAAAAGAAG  5371
Rat Ch3 trim       5341 TTAGATCGGGACAGACAATATTGCTGAGGATTTATCTGAAGGTGTCAAAAGGAGAAGAAG  5400
M Mus Ch2 trim     6338 TTAGATGGGGAAAGACAGT-CTGCTGAGGATTTATCTGGAACTGTCAGAAGGAAAAGAAG  6396
H. Sap. Ch20 tr    6325 CTGAATGGGGAAAGACAATA-TGCTAACAAGTTATCTGAGGGTGTCAGAAAGAAATGATG  6383
                         *  ** **** ***              * *******    ***** ** ** * ** *

EESYR              5372 GGAAACAGG-CACTTGGGA-AAATGTCCTCCCGCCCACCCGAATTTTGGCTT-GGCAACC  5428
Rat Ch3 trim       5401 GGAAACAGGGCACTCAGGG-AAATGGCCTCTAGTCT----GAGTTCTGGCTC-AGCAACA  5454
M Mus Ch2 trim     6397 GTAAATGGGGCACTTGGGA-AAGTGGCCTCTAGTTT----GACTTCTGGCTT-AGCAAAG  6450
H. Sap. Ch20 tr    6384 AAAAACAGTACAGTTGGGGGAAATGTTTTCCAGCCT----GCTTTCTGGTTTTAGCGACT  6439
                          ***  *  ** *  **  ** **   **  *       *  ** *** *   ** *

EESYR              5429 GT-GGTGGAGGAGCAAGAAACACGTGGACGTTTGA-GGAGGCAT-GGGGTCCTAGGAGGA  5485
Rat Ch3 trim       5455 GA-GGTGGGGAGATAAGGCACACACAGTGGTTAGAAGGAGTCATCAGGGTTCTGGGAGGA  5513
M Mus Ch2 trim     6451 GT-TGTGGGGAGATAAGGCATACACAGTAGTTAGCAGGAGGCAACAGGGTCCTGGGAGGA  6509
H. Sap. Ch20 tr    6440 GCATGGGAAGAGATAAGACACACATGGCTTTTATAAGGAGCCATCGGGATCTCTAGGGGA  6499
                        *   * *  *    ***  * **   *    **   **** **   ** *     * ***

EESYR              5486 CAGGAAGCAGAAGGAGAGAGCTGGGCTGACAGCCTGCAGGCATTGCACAGTTTC--AGAA  5543
Rat Ch3 trim       5514 CAGGAGGCAGGAG----AGGCAGGGCTGACAGTGTGCAATCATTGTGTAGTCTC--CCAA  5567
M Mus Ch2 trim     6510 CGCGAGGCAGAAGGAG-AGGCTGGGCTGACAGCATGCAATCATTGCATAGTCTC--CAAA  6566
H. Sap. Ch20 tr    6500 CATGAGGCAGGAGAAAAGAATTGGGCTGAAAGCATCCAATCATCACATATTCACGGAGAA  6559
                        *  ** **** **         ******* **  * **  ***     * *  *    **

EESYR              5544 GGAGATTACAGCATGACTGAG------TTTTTAGGGATCCAACAGGGACCTG---GGTAG  5594
Rat Ch3 trim       5568 GGAGATTACAACATGGCTGAA------TTTTCAGGGGTCCAACGGAGACTGT---AGTGG  5618
M Mus Ch2 trim     6567 GGAGATTGCAACATGGCTGAG------TTTTCAGAGGTCCTACAGAGCCCGT---GGTAG  6617
H. Sap. Ch20 tr    6560 AGAGATTACAATATAGCAGAGGAAGCTCTTCCAGGGCTCCTACAGGGACCTTTGGGACAA  6619
                         ****** **  **  * **        **  ** * *** ** * * *
EESYR              5595 AGATTCTGTGGGCTCTGAGGCAACTTGACCTCAGCCAGATGGTATTTGAATAACCTGCTC  5654
Rat Ch3 trim       5619 AGATTCTGTGGGTTCTGAGACAACTTGACTTCAGCCAGATGGCATTTGAATAAC------  5672
M Mus Ch2 trim     6618 AGATTCTGTGGGTTCTGAGACAACTTGACTTTAGCCAGATGGTATTTGAGTAATCTGGG-  6676
H. Sap. Ch20 tr    6620 AGATTCAGTGGGCTTTGGGACAGCTTGACTTCAACTAGATGGTATTTGAATAATCTGCT-  6678
                        ****** ***** * ** * ** ****** * * * ****** ****** ***
```

Fig. 3B

```
EESYR              5655 TTAGAGGGAAAACAGACATAGCAAACAGAGCCACGTTTAGTGATGAAACTCTCACTTTGC  5714
Rat Ch3 trim       5673 -------------AGCTCCAGCAAGCACAGCCACATTTAGGGATGAAACTCTCACTTTGA  5719
M Mus Ch2 trim     6677 --AGAGAGAAAACAGCTACAGCAAACAGGGCCACATTTAGTGACGAAACTCTCACTTTGA  6734
H. Sap. Ch20 tr    6679 --GGAGAGAAAACAGATATAGCACACACTGTCACATTTAGCGTTGAAACTCTCGGTTTGA  6736
                                     **    ****  **  * *** ***** *  *********  ****

EESYR              5715 CTG---AGTCATGTGCGGCCATGCCCAGGGGTCAGGCTGACACTCAACTCAAAAACAAGT  5771
Rat Ch3 trim       5720 CTGT-GAGTCACGTGTAGCTGTGTCCCGAGGTCAGGCTGGCCCTCAGCTCAAAAACAAGT  5778
M Mus Ch2 trim     6735 CTGTTGAGTCATTTGCAG-TGGGCCCTGAGGTCAGGCTGGCCCTCAGCTCAAAAACAAGC  6793
H. Sap. Ch20 tr    6737 CTAT-GAGTAATGTTCAGCCATGCCCAAGGGTCAGGCCTACACTCA-CTCAGAAACAAGT  6794
                        **    *** *  *   *    * **   ********   * **** **** *******

EESYR              5772 GAGAAATTGAAG-----------ACAATCCGTGGTGGCAGCTACTGGAA-GGGCCACCAC  5819
Rat Ch3 trim       5779 GAGGGATTGAAGCAATTACTCAGATAATTCACAGCCACAGCTACGGGGA-GGGCCGC---  5834
M Mus Ch2 trim     6794 GAGGAACTGAAGCAATTACTCAGATAATCCACAGCCACAGCCACTGGAAAGGGCCAC---  6850
H. Sap. Ch20 tr    6795 GGGGAATTGAAGCAATTATTCAGATAATCCATAGACATAGCTACTGGCCAGTGCTGC---  6851
                        * *  * *****           * *** *   *    *** ** **   * **  *

EESYR              5820 ATCCCCAGAAAGAGT------GGAGCTGCTAAAAAGCCAT--------TTGTGATAGGCA  5865
Rat Ch3 trim       5835 ATCCCCAGAAACATC------GGGGTTACTATAAAGCTA-----------GTGGTGGTCA  5877
M Mus Ch2 trim     6851 ATCCCCAGAGACAGCACAGCAGGGGTGGGGGTGGGGCTATGAGAAAGTTAGTGATTGTAG  6910
H. Sap. Ch20 tr    6852 -ACCCCTGATTTAGCCCA---GAAACAGTAATGCTATTATAAGCT-GTTGGTGATTTGTG  6906
                          **** **   *        *                *           *** *

EESYR              5866 CAGTTATCTTGAATGCATGGAGCAGAG---ATTACGGAAAAATCGAGAATGTTAATGAGG  5922
Rat Ch3 trim       5878 CAGTTATCTTGAATGTATGGAGCAGAGGAGATTACAGAAAAACCTAGAATGTTAATGAGG  5937
M Mus Ch2 trim     6911 CAGTTATCTAGAATGTGCGGAGCAGAGGAGGTTACACAAAAACCTAGAATG---------  6961
H. Sap. Ch20 tr    6907 GAGCAATCTTGAATTTATTAAGGAAAGGAGATTATAGAAAAATCCAGAATGCCAATG-GG  6965
                         **  **** ****      ** * **    *** ***** * ******
```

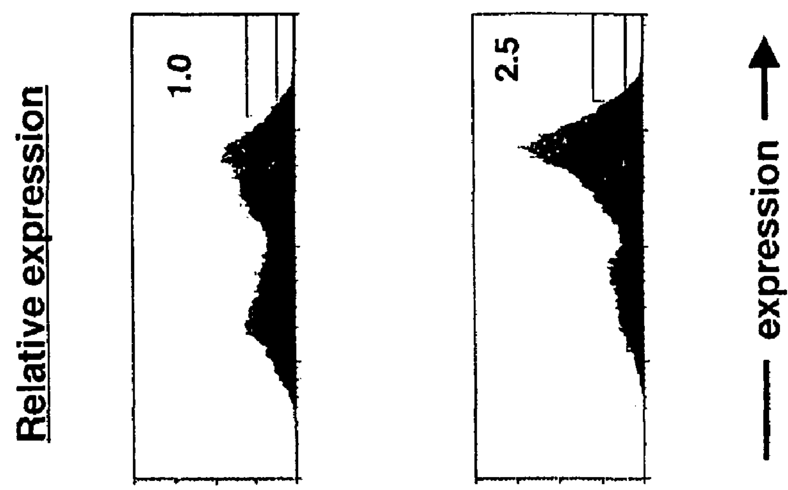
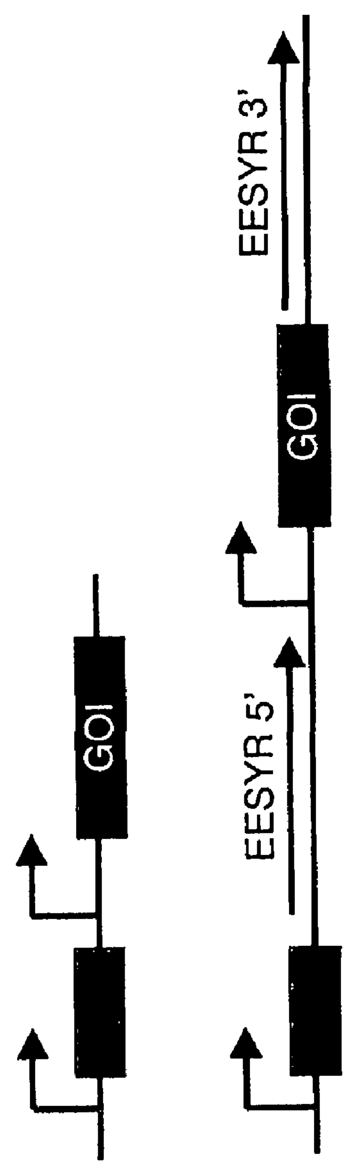
Fig. 5

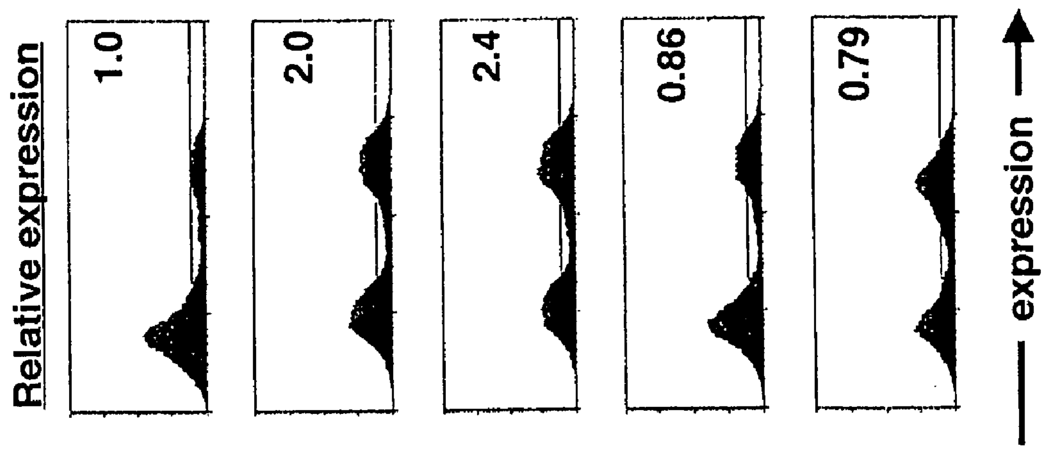
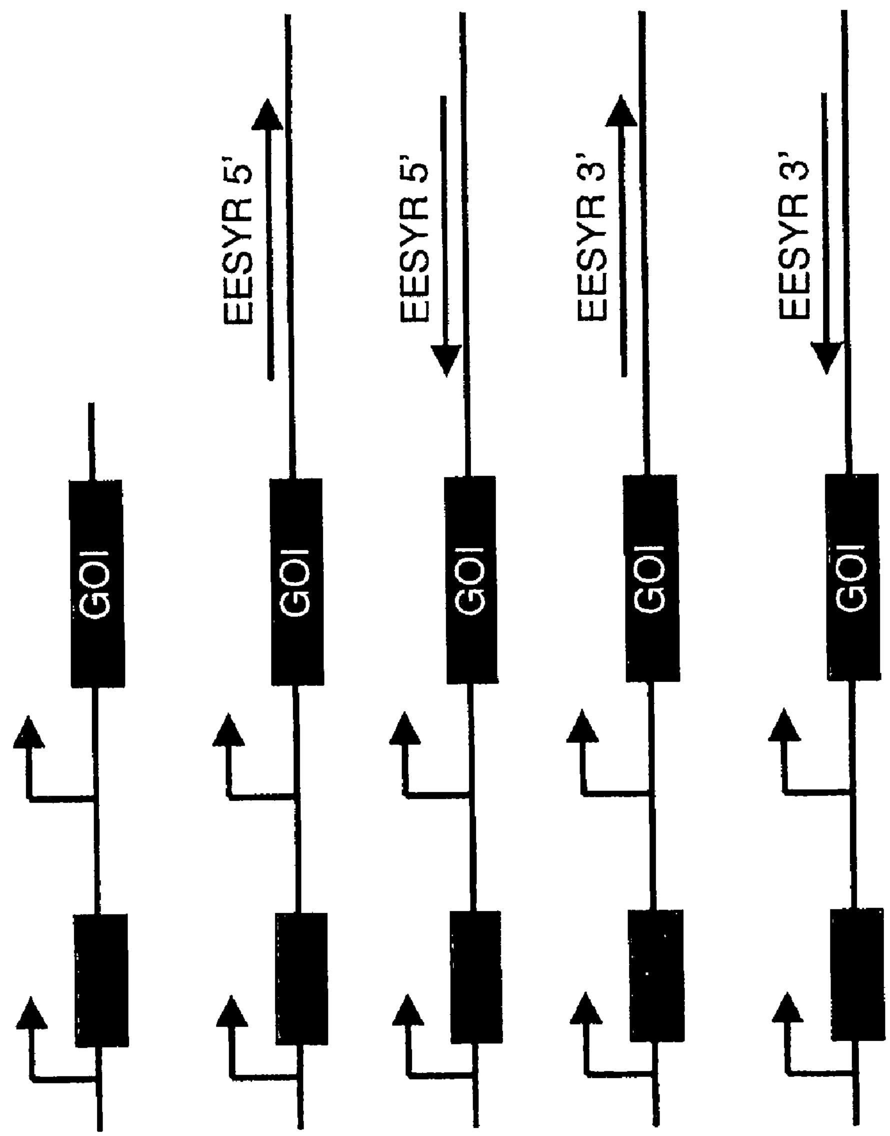
Fig. 6

Promoter "B"
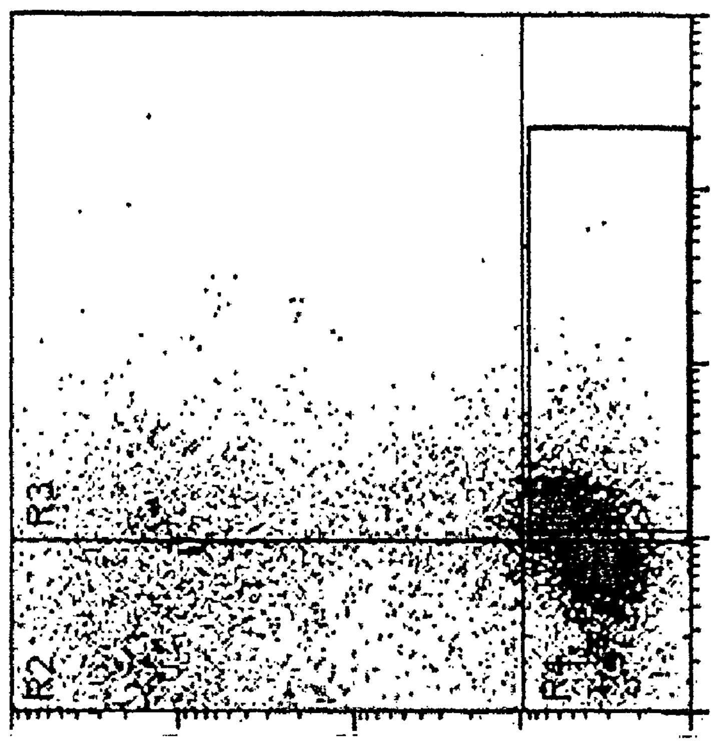
1
Promoter "A"
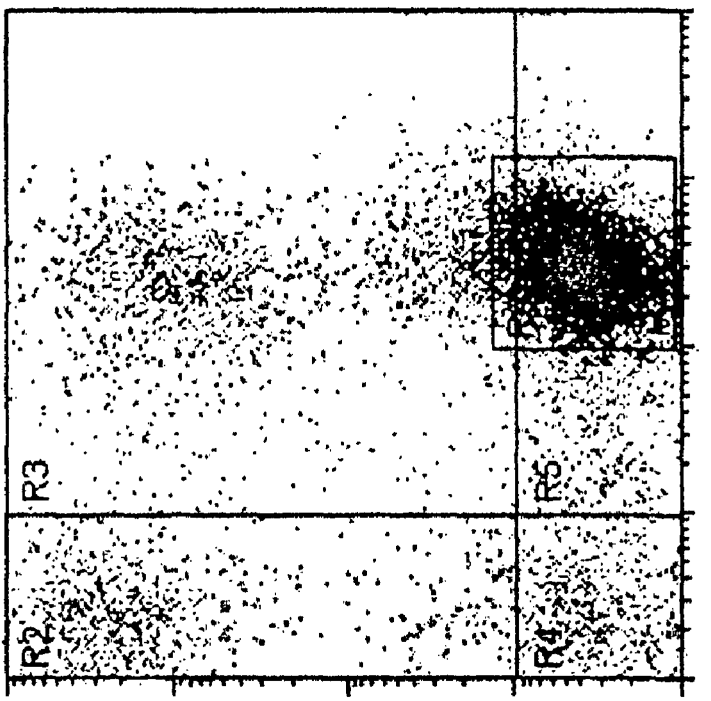
Relative expression: 16
Fig. 10

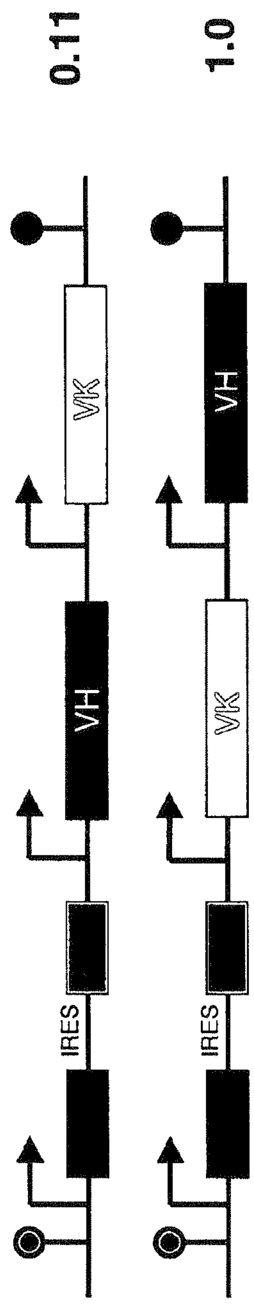
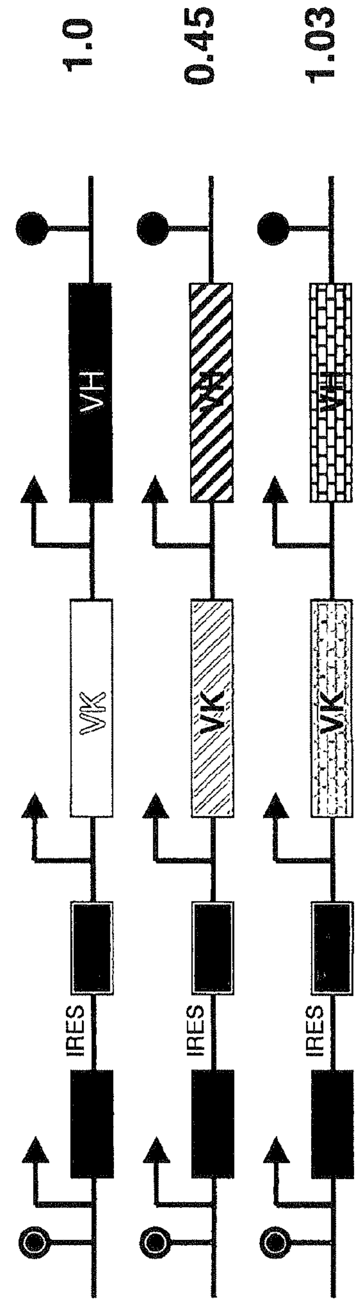
Fig. 12

SEQUENCE LISTING

```
<160> NUMBER OF SEQ ID NOS: 8

<210> SEQ ID NO 1
<211> LENGTH: 6473
<212> TYPE: DNA
<213> ORGANISM: Cricetulus griseus
```

<400> SEQUENCE: 1

```
tctagaaaca aaaccaaaaa tattaagtca ggcttggctt caggtgctgg ggtggagtgc      60
tgacaaaaat acacaaattc ctggctttct aaggcttttt cggggattca ggtattgggt     120
gatggtagaa taaaaatctg aaacataggt gatgtatctg ccatactgca tgggtgtgta     180
tgtgtgtgta tgtgtgtctg tgtgtgtgcc cagacagaaa taccatgaag gaaaaaaaca     240
cttcaaagac aggagagaag agtgacctgg gaaggactcc ccaatgagat gagaactgag     300
cacatgccag aggaggtgag gactgaacca ttcaacacaa gtggtgaata gtcctgcaga     360
cacagagagg gccagaagca ctcagaactc cagggggtca ggagtggttc tctggaggct     420
tctgcccttg gaggttcctg aggaggaggc ttccatattg aaaatgtagt tagtggccgt     480
ttccattagt acagtgacta gagagagctg agggaccact ggactgaggc ctagatgctc     540
agtcagatgg ccatgaaagc ctagacaagc acttccgggt ggaaaggaaa cagcaggtgt     600
gaggggtcag gggcaagtta gtgggagagg tcttccagat gaagtagcag gaacggagac     660
gcactggatg gccccacttg tcaaccagca aaagcttgga tcttgttcta agaggccagg     720
gacatgacaa gggtgatctc ggtttttaaa aggctttgtg ttacctaatc acttctatta     780
gtcagatact ttgtaacaca aatgagtact tggcctgtat tttagaaact tctgggatcc     840
tgaaaaaaca caatgacatt ctggctgcaa cacctggaga ctcccagcca ggccctggac     900
ccgggtccat tcatgcaaat actcagggac agattcttca ctaggtactg atgagctgtc     960
ttggatgcaa atgtggcctc ttcattttac tacaagtcac catgagtcag gaggtgctgt    1020
ttgcacagtg tgactaagtg atggagtgtt gactgcagcc attcccggcc ccagcttgtg    1080
agagagatcc ttttaaattg aaagtaagct caaagttacc acgaagccac acatgtataa    1140
actgtgtgaa taatctgtgc acatacacaa accatgtgaa taatctgtgt acatgtataa    1200
actgtgtgaa taatctgtgt gcagcctttc cttacctact accttccagt gatcaggttt    1260
ggactgcctg tgtgctactg gaccctgaat gtccccaccg ctgtcccctg tcttttacga    1320
ttctgacatt tttaataaat tcagcggctt cccctctgct ctgtgcctag ctataccttg    1380
gtactctgca ttttggtttc tgtgacattt ctctgtgact ctgctacatt ctcagatgac    1440
atgtgacaca gaaggtgttc cctctggaga catgtgatgt ccctgtcatt agtggaatca    1500
gatgccccca aactgttgtc cagtgtttgg gaaagtgaca cgtgaaggag gatcaggaaa    1560
agaggggtgg aaatcaagat gtgtctgagt atctcatgtc cctgagtggt ccaggctgct    1620
gacttcactc ccccaagtga gggaggccat ggtgagtaca cacacctcac acatactata    1680
tccaacacac acacacacac acacacacac acgcacgcac gcacgcacgc acgcacacat    1740
gcacacacac gaactacatt tcacaaacca catacgcata ttacacccca aacgtatcac    1800
ctatacatac cacacataca caccccctcca cacatcacac acataccaca cccacacaca    1860
gcacacacat acataggcac acattcacac accacacata tacatttgtg tatgcataca    1920
tgcatacaca cacaggcaca cagacaccac acacatgcat tgtgtacgca cacatgcata    1980
cacacacata ggcacacatt gagcacacac atacatttgt gtacgcacac tacatagaca    2040
tatatgcatt tgtatatgca cacatgcatg cacacataca taggcacaca tagagcacac    2100
acatacattt gtgtatgcac acatgcacac accaatcaca tgggaagact caggttcttc    2160
actaaggttc acatgaactt agcagttcct ggttatctcg tgaaacttgg aagattgctg    2220
tggagaagag gaagcgttgg cttgagccct ggcagcaatt aaccccgccc agaagaagta    2280
```

-continued

```
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctattttgtt atatctttat taaatattct tttagtttta   2460
tgtgcgtgaa taccttgctt gcataaatgt atgggcactg tatgtgttct tggtgccggt   2520
ggaggccagg agagggcatg gatcctccgg agctggcgtt tgagacagtt gtgacccaca   2580
gtgtggggtc tgggaactgg gtcttagtgt tccgcaagtg cagctggggc tcttaacctc   2640
tgagccatcc ctccagcttc aagaaactta ttttcttagg acatggggga agggatccag   2700
ggctttaggc ttgtttgttc agcaaatact cttttcgtgt attttgaatt ttattttatt   2760
ttactttttt gggatagaat cacattctgc agctcaggct gggcctgaac tcatcaaaat   2820
cctcctgtct cagtctacca ggtgataaga ttactgatgt gagcctggct ttgacaagca   2880
ctttagagtc cccagccctt ctggacactt gttccaagta taatatatat atatatatat   2940
atatatatat atatatatat atatattgtg tgtgtgtgtt tgtgtgtgta tgagacactt   3000
gctctaaggg tatcatatat atccttgatt tgcttttaat ttatttttta attaaaaatg   3060
attagctaca tgtcacctgt atgcgtctgt atcatctata tatccttcct tccttctctc   3120
tctttctctc ttcttcttct cacccccaag catctatttt caaatccttg tgccgaggag   3180
atgccaagag tctcgttggg ggagatggtg agggggcgat acaggggaag agcaggagga   3240
aagggggaca gactggtgtg ggtctttgga gagctcagga gaatagcagc gatcttccct   3300
gtccctggtg tcacctctta cagccaacac cattttgtgg cctggcagaa gagttgtcaa   3360
gctggtcgca ggtctgccac acaaccccaa tctggcccca agaaaaggca cctgtgtgtg   3420
actctggggt taaaggcgct gcctggtcgt ctccagctgg acttgaaact cccgtttaat   3480
aaagagttct gcaaaataat acccgcagag tcacagtgcc aggttcccgt gctttcctga   3540
agcgccaggc acgggttccc taggaaatgg ggccttgctt gccaagctcc cacggcttgc   3600
cctgcaaacg gcctgaatga tctggcactc tgcgttgcca ctgggatgaa atggaaaaaa   3660
gaaaaagaag aagtgtctct ggaagcgggc gcgctcacac aaacccgcaa cgattgtgta   3720
aacactctcc attgagaatc tggagtgcgg ttgccctcta ctggggagct gaagacagct   3780
agtgggggcg gggggaggac cgtgctagca tccttccacg gtgctcgctg gctgtggtgc   3840
atgccgggaa ccgaaacgcg gaactaaagt caagtcttgc tttggtggaa ctgacaatca   3900
acgaaatcac ttcgattgtt ttcctctttt tactggaatt cttggatttg atagatgggg   3960
gaggatcaga gggggagggg aggggcgggg agacggaggg aggaggggag gaggggagga   4020
ggggaggagg ggaggagggg aagggatgga ggaaaatact aacttttcta attcaacatg   4080
acaaagattc ggagaaagtg caccgctagt gaccgggagg aggaatgccc tattgggcat   4140
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcac tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggccctt ggtgagattt ctttgtgtat   4440
ttatttagag acagggtctc atactgtagt ccaagctagc ctccagctca cagaaattct   4500
cctgttccgg tttccaaagt actggagtta tgagtgtgtg ttaattgaac gctaagaatt   4560
tgctgattga agaaaacctc aagtgggttt ggctaatccc cacgacccca gaggctgagg   4620
caggaggaat gagagaattc aaggtttgcc agagccacag ggtgagctca atgtggagac   4680
```

-continued tgtgagggtg agctcaatgt ggagactgtg agggtgagct caatgtggag actgtgaggg 4740
tgagctcaat gtggagactg tgagggtgag ctcaatgtgg agactgtgag ggtgagctca 4800
atgtggagac ctgtatcaag ataataatag tagtagtaac aatgcaggcg agggtgtggt 4860
tgagtggtag agcagttagt tgatttgaca tgcttgaggt ctcccggtcc atctgtggcc 4920
ctgcaacagg aagggaggga ggaagggggg gaacgagaga gaggaaagag agacagaagc 4980
taagataggg aatgagagag gaaggaagaa acgggaagaa attcagactc cttcctgagt 5040
tccgccaacg cctagtgaca tcctgtgcac accctaaggt ggcctttgtg tggcactggc 5100
ttgggtggtc gggaaaggca ttttcagctt gttgcagaac tgccacagta gcatgctggg 5160
tccgtgaaag tttctgcccg ttaacaagaa gtctctacta cttgtgacct caccagtgaa 5220
aatttcttta attgtctcct ggtgttctgg gttttgcatt tttgtttcta aggatacatt 5280
cctgggtgat gtcatgaagt ccccaaagac acagtggggc tgtgttggat tgggaaagat 5340
gatttatctg ggtgtcaaa aggaaaagaa gggaaacagg cacttgggaa aatgtcctcc 5400
cgcccacccg aattttggct tggcaaccgt ggtggaggag caagaaacac gtggacgttt 5460
gaggaggcat ggggtcctag gaggacagga agcagaagga gagagctggg ctgacagcct 5520
gcaggcattg cacagtttca gaaggagatt acagcatgac tgagttttta gggatccaac 5580
agggacctgg gtagagattc tgtgggctct gaggcaactt gacctcagcc agatggtatt 5640
tgaataacct gctcttagag ggaaaacaga catagcaaac agagccacgt ttagtgatga 5700
aactctcact ttgcctgagt catgtgcggc catgcccagg ggtcaggctg acactcaact 5760
caaaaacaag tgagaaattg aagacaatcc gtggtggcag ctactggaag ggccaccaca 5820
tccccagaaa gagtggagct gctaaaaagc catttgtgat aggcacagtt atcttgaatg 5880
catggagcag agattacgga aaaatcgaga atgttaatga ggcaacattc gagttgagtc 5940
attcagtgtg ggaaacccag acgcttccat cccctaaaag gaacatcttg ctctcagtca 6000
aaatggaaat aaaaattggg gcttgaattt ggcaaatgat tcagaactct gtgtaggtat 6060
tttcacacgc acagtggata attttcatgt tggagtttat ttgtgctaaa aggcagaaaa 6120
gggtaaaaag cacatcttaa gagttatgag gttctacgaa taaaaataat gttacttaca 6180
gctattcctt aattagtacc cccttccacc tgtggtaatt tcctgagata gtcagtgggg 6240
aaaagatctc tccttctctt ctttctcccc ctcccctcct ctccctccct ccctccctcc 6300
ctccctcctc tccctccctc cccctttcct tctttctttg ctccttctcc tctgcctcct 6360
tctccctttc ttcttcattt attctaagta gcttttaaca gcacaccaat tacctgtgta 6420
taacgggaaa acacaggctc aagcagctta gagaagattg atctgtgttc act 6473

<210> SEQ ID NO 2
<211> LENGTH: 7045
<212> TYPE: DNA
<213> ORGANISM: Cricetulus griseus

<400> SEQUENCE: 2
actagcgtgc aattcagagg tgggtgaaga taaaaggcaa acatttgagg ccatttcctt 60
atttggcacg gcacttagga agtggaacat gcctaatcta ctggtttgta ccacctttcc 120
ctataatgga ctgtttggga agctcctggg caaccgattc tggcatctca ttggtcagag 180
gcctgttaaa tggtactctt atttgcaaag aaggctgtaa cttgtagctt taaaagcctc 240
tcctcaagaa agaagggaga aaggatatgg ctagacatat ctaatagact taaccactgt 300

-continued

```
gaaaagcctt agtatgaatc agatagaacc tatttttaac tcagttttga aaaaaataat    360
ctttatattt atttgtgtgt gtgtgtgtgt gtgtgtgtgt gtgtgtgtgt gtgtgtgtgt    420
gaaccacatg tagcaggtgc tggaggaggc cagaagaggg caccagatct cctggaactg    480
acaccacaca tggttatgag ctgcctgatg tgggtgctgg gaactgaact ctcgtgttct    540
gcaagagcag caactgttct cttaactgat gagccatctc tccagccccc cccataattt    600
taattgttca ttttagtaaa ttttattcat aatcaattat cacagtataa aacaatgatt    660
ttatatatat catatacata tcaaggatga cagtgagggg gatatgtgtg tgtgtgtgtg    720
tgtgtgtgtg tgtgtgtgtg tgtgttattt gtgtgtgtgc tttttaagaa ggtgccatag    780
tcactgcatt tctctgaagg atttcaaagg aatgagacat gtctgtctgc caggaaccct    840
atcttcctct ttgggaatct gacccaaatg aggtattctg aggaactgaa tgaagagctc    900
aagtagcagt gtcttaaacc caaatgtgct gtctagagaa agtcaacgtc atcagtgagc    960
tgaggagaga tttactgagc ggaagacaag cgctctttga tttaagtggc tcgaacagtc   1020
acggctgtgg agtggagcct gtgctcaggt ctgaggcagt ctttgctagc cagctgtgat   1080
gagcagtgaa gaaagggtgg agatggaggc agggtgggag cagggctatg gttcagacta   1140
ggtatcgtga gcacaccagc tggttgactt gtggtctgtg ggtcaggcgt tgtaaacgcc   1200
ctcagggtca ggcagtcaca ttgcttgaag ctgaatgggt gaggcaacac agagagtgca   1260
aagaaggcaa agtaccacct cttccccgac ccaggtcact tctgggttat agctgagact   1320
ccggacagca tgcaaccagc tggttagagc ttcagggaaa acttgatgtc tgcatgttgc   1380
tatgaaatgt gattcggtac atctggagaa aatttataat gctggctcag tcaagcactg   1440
aacaaaggta ccttggcttt gggagctaca tgacattgac ttgtaggcag actttttttt   1500
ttctgcccgc caattcccag ataaccaata tggaggctca atattaatta taaatgctcg   1560
gctgatagct caggcttgtt actagctaac tcttccaact taaatgaacc catttctatt   1620
atctacattc tgccacgtga ctttaccttg tacttcctgt ttcctctcct tgtctgactc   1680
tgcccttctg cttcccagag tccttagtct ggttctcctg cctaacctta tcctgcccag   1740
ctgctgacca agcatttata attaatatta agtctcccag tgagactctc atccagggag   1800
gacttgggtg ctccccccctc ctcattgcca tccgtgtctt cctcttccct cgcttccccc   1860
tcctcttcct gctcttcctc ctccacccct cctttcatag tattgatggc aagggtgttc   1920
tagaatggag gagtgcccat aggcatgcaa agaaaccagt taggatgctc tgtgaggggt   1980
tgtaatcata agcgatggac acaattcaag ccacagagtg aagacggaag gatgcactgt   2040
gctctagagc aacttctggg gcagaatcac agggtgagtt tctgacttga gggcgaagag   2100
gccacgagga agggagtgag tttgtctgag ctagaagcta cggcccacct cttggtagca   2160
gacctgccca caagcatgct ttgttaatca tgtgggatct gattttcctc taaatctatg   2220
ttcaactctt aagaaaatgt gaattctcac attaaaattt agatatacgt cttttggtgg   2280
ggggggtgta aaaaatcctc aagaatatgg atttctgggg gccggagaga tggctcagag   2340
gttaagagaa ctggttgctc ttctagacat tctgagttca attcccagca accacatggt   2400
ggctcacaac catctgtaat gcgacctggt gccatcttct gacatgcatg gatacatgca   2460
ggcagaaagc tgtatacata gtaaattgat aaatcttttt ttaaaaagag tatggattct   2520
gccgggtgtt ggtggcgcac gcctttaatc ccagcactct ggaggcagag gcaggtggat   2580
ctctgtgagt tcgagaccag cctggtctat aagagctagt tccaggacag cctccaaagc   2640
cacagagaaa ccctgtctcg aaaaaccaaa aaaaaaaaaa aaaaaaaaaa aaaaaaaaga   2700
```

-continued

```
gtatggattc taagaaagcc gtaacagctg gagctgtgta cggagttcag cgtggtacta   2760
gaagaacaga cattcatgat gaaacacccc aggattttta cttagtatct agtttccatt   2820
gttgttttga gaccggctct tatgctctcc aggctggcct caaactgctg atcttcccgc   2880
ctctacctct caagtcctgg gactacttgg ctcataaaac agtttttgtc gggctccctg   2940
aagttatggt tgtacaaacc gtgggggtca atatactcac ttgggcagag agagaaggtc   3000
tgaatcccag acaatgactg catctcagga cagttgggaa gaggacaatg gcagaaggac   3060
ttagaaaaga tagactggag ggtggaaaag cagcaggaac agagaaacaa aacaggaagc   3120
ttgctatcca gggccactct ggagtcctgt ggcaagatgg aagcgggcta ggggaataca   3180
tttgtgctac tgtgtgtgtg tgtgtgtgtg tgtgtgtgtg tgtgtgtgat caatgcctat   3240
caatgttgaa ggggaaatat gtataccaca ttgattctgg gagcaattct cagtatctgg   3300
cctagagaaa ggaatggccc ctgcagaata gacagagtga atggtgccct ttatcatttg   3360
ctaaagtgaa ggagaaataa acatccttcc atagagtttc aggtaaatga accccacagt   3420
tcatctgtgc cgtggtggag gcctggccaa cagttaaaaa gattagacac ggacaaagtc   3480
tgaaggaaac acctcgaata ggaagaggag agccacctca ttctgtaact ttcctcaagg   3540
ggaagatgtt ccaagagtgg gaataaatgg tcaaaggggg gatttttaat taggaaaacg   3600
atttcctgta tcacttgtga aactggaggt tgatttgggg cataggacaa tagatttgat   3660
gctttgcaaa aagctgtttc aaagcagaga aatggaatag agacaattat gtagcgagga   3720
gggagggtgg ggcgaagatg gagacagaga agtggaagct gactttaggg aagaggaaca   3780
tagaccacag gggcggggcg gggggcaggg gcgggggggcg gggctcaaag gaggcagtgg   3840
gaacgttgct agtgttcgca gcgtaagcgt gaatgtgcaa gcgtctttgt ggtgtgtgac   3900
caggagtagc gtggctggct tgtgtgctgc ttgtaatccc agtctttgag gtttccacac   3960
tgttccacag tgggtgtgat tttccctcgg agagcatgag ggctctgctt tccccacatc   4020
ctccccagcg ttcgttggta tttgtttcca agatgttagt gggtgagaca aagcctctct   4080
gttgatttgc ctttaacagg tgacaaaaaa agctcaacca ggagacattt ttgccttctt   4140
ggaaggtaat gctcccatgt agagcaatgg gacccatctc taaggtgagg ctactcttgc   4200
agtttgcacc cagctcttct gatgcaggaa ggaagttggt gggcaagcaa gactgtttgc   4260
ttcttgcgat ggacacattc tgcacacaaa ggctcaggag gggagaaggc tgtttgatgt   4320
ttagcactca ggaaggcccc tgatgcatct gtgattagct gtctccatct gtggagcaga   4380
cacggactaa ctaaaaacca gtgtttttaa attgtcaagc ctttaaggtg aggaaattga   4440
cttattgtgc tgggccatac gtagagcaag tgctctgcat tgggccaacc cccggctctg   4500
gtttctaggc accagaatgg cctagaacta actcacaatc ctcccattcc aggtctcagg   4560
tgctagaatg aaccactata ccagcctgcc tgcctgccta cctgccttcc taaattttaa   4620
atcatgggga gtaggggaga atacacttat cttagttagg gtttctattg ctgtgaagag   4680
acaccatgag catggcaact cttataaagg aaaacattta gttgggtggc agtttcagag   4740
gttttagtac attgtcatca tggctgggaa catgatggca tgcagacaga catggtgctg   4800
gagaaaggga tgagagtcct acatcttgca ggcaacagga cctcagctga gacactggct   4860
ggtaccctga gcataggaaa cctcacagcc caccctcaca gtgacatatt tccttcaaca   4920
aagccatacc tcctaatagt gccactccct atgagatgac agggccaatt acattcaaac   4980
tgctataaca ctttaaagta ttttattttt attattgtaa attatgtatg tagctgggtg   5040
```

-continued

```
gtggcagccg aggtgcacgc ctttaatccc agcacttggg aggcagaggc agatggatct   5100

ctgtgagttc aagaccagcc tggtctataa gagctagttg caaggaagga tatacaaaga   5160

acagttctag gatagccttc aaagccacag agaagtgctg tcttgaaaac caaaaattgt   5220

gctgggacct gtctctgctt tggttgcttc ccactccccc agagctggac tcttggtcaa   5280

cactgaatca gctgcaaaat aaactcctgg attcctctct tgtaacagga gcccgaagtc   5340

aggcgcccac ttgtcttctc gcaggattgc catagacttt ttctgtgtgc ccaccattcc   5400

agactgaagt agagatggca gtggcagaga ctgggaaggc tgcaacgaaa acaggaagtt   5460

attgcaccct gggaatagtc tggaaatgaa gcttcaaaac ttgcttcatg ttcagttgta   5520

cacagactca ctcccaggtt gactcacacg tgtaaatatt cctgactatg tctgcactgc   5580

ttttatctga tgcttccttc ccaaaatgcc aagtgtacaa ggtgagggaa tcacccttgg   5640

attcagagcc cagggtcgtc ctccttaacc tggacttgtc tttctccggc agcctctgac   5700

acccctcccc ccattttctc tatcagaagg tctgagcaga gttggggcac gctcatgtcc   5760

tgatacactc cttgtcttcc tgaagatcta acttctgacc cagaaagatg gctaaggtgg   5820

tgaagtgttt gacatgaaga cttggtctta agaactggag caggggaaaa aagtcggatg   5880

tggcagcatg tacccgaaat cccagaactg gggaggtaga gacggatgag tgcccggggc   5940

tagctggctg ctcagccagc ctagctgaat tgccaaattc caactcctat tgaaaaacct   6000

ttaccaaaca aacaaacaaa caaataataa caacaacaac aacaacaaac taccccatac   6060

aaggtgggcg gctcttggct cttgaggaat gactcaccca aacccaaagc ttgccacagc   6120

tgttctctgg cctaaatggg gtgggggtgg ggcagagaca gagacagaga gagacatgac   6180

ttcctgggct gggctgtgtg ctctaggcca ccaggaactt tcctgtcttg ctctctgtct   6240

ggcacagcca gagcaccagc acccagcagg tgcacacacc tccctccgtg cttcttgagc   6300

aaacacaggt gccttggtct gtctattgaa ccggagtaag ttcttgcaga tgtatgcatg   6360

gaaacaacat tgtcctggtt ttatttctac tgttgtgata aaaaccgggg aactccagga   6420

agcagctgag gcagaggcaa atgcaaggaa tgctgcctcc tagcttgctc cccatggctt   6480

gccgggcctg ctttctgcaa gcccttctct ccccattggc atgcctgaca tgaacagcgt   6540

ttgaaatgct ctcaaatgtc actttcaaag aaggcttctc tgatcttgct aactaaatca   6600

gaccatgttt caccgtgcat tatctttctg ctgtctgtct gtctgtctgt ctgtctatct   6660

gtctatcatc tatcaatcat ctatctatct atcttctatt tatctaccta tcattcaatc   6720

atctatcttc taactagtta tcatttattt atttgtttac ttactttttt tatttgagac   6780

agtatttctc tgagtgacag ccttggctgt cctggaaccc attctgtaac caggctgtcc   6840

tcaaactcac agagatccaa ctgcctctgc ctctctggtg ctggggttaa agacgtgcac   6900

caccaacgcc ccgctctatc atctatttat gtacttatta ttcagtcatt atctatcctc   6960

taactatcca tcatctgtct atccatcatc tatctatcta tctatctatc tatctatcta   7020

tctatcatcc atctataatc aattg                                         7045
```

```
<210> SEQ ID NO 3
<211> LENGTH: 6473
<212> TYPE: DNA
<213> ORGANISM: Cricetulus griseus

<400> SEQUENCE: 3

agtgaacaca gatcaatctt ctctaagctg cttgagcctg tgttttcccg ttatacacag     60

gtaattggtg tgctgttaaa agctacttag aataaatgaa gaagaaaggg agaaggaggc    120
```

-continued

```
agaggagaag gagcaaagaa agaaggaaag ggggagggag ggagaggagg gagggaggga    180
gggagggagg gagaggaggg gagggggaga aagaagagaa ggagagatct tttccccact    240
gactatctca ggaaattacc acaggtggaa gggggtacta attaaggaat agctgtaagt    300
aacattattt ttattcgtag aacctcataa ctcttaagat gtgcttttta ccctttttctg   360
ccttttagca caaataaact ccaacatgaa aattatccac tgtgcgtgtg aaaataccta    420
cacagagttc tgaatcattt gccaaattca agccccaatt tttatttcca ttttgactga    480
gagcaagatg ttccttttag gggatggaag cgtctgggtt tcccacactg aatgactcaa    540
ctcgaatgtt gcctcattaa cattctcgat ttttccgtaa tctctgctcc atgcattcaa    600
gataactgtg cctatcacaa atggcttttt agcagctcca ctctttctgg ggatgtggtg    660
gcccttccag tagctgccac cacggattgt cttcaatttc tcacttgttt ttgagttgag    720
tgtcagcctg accoctgggc atggccgcac atgactcagg caaagtgaga gtttcatcac    780
taaacgtggc tctgtttgct atgtctgttt tccctctaag agcaggttat tcaaatacca    840
tctggctgag gtcaagttgc ctcagagccc acagaatctc tacccaggtc cctgttggat    900
ccctaaaaac tcagtcatgc tgtaatctcc ttctgaaact gtgcaatgcc tgcaggctgt    960
cagcccagct ctctccttct gcttcctgtc ctcctaggac cccatgcctc ctcaaacgtc   1020
cacgtgtttc ttgctcctcc accacggttg ccaagccaaa attcgggtgg gcgggaggac   1080
attttcccaa gtgcctgttt cccttctttt ccttttgaca ccccagataa atcatctttc   1140
ccaatccaac acagccccac tgtgtctttg gggacttcat gacatcaccc aggaatgtat   1200
ccttagaaac aaaaatgcaa aacccagaac accaggagac aattaaagaa attttcactg   1260
gtgaggtcac aagtagtaga gacttcttgt taacgggcag aaactttcac ggacccagca   1320
tgctactgtg gcagttctgc aacaagctga aaatgccttt cccgaccacc caagccagtg   1380
ccacacaaag gccaccttag ggtgtgcaca ggatgtcact aggcgttggc ggaactcagg   1440
aaggagtctg aatttcttcc cgtttcttcc ttcctctctc attccctatc ttagcttctg   1500
tctctctttc ctctctctcg ttccccccct tcctccctcc cttcctgttg cagggccaca   1560
gatggaccgg gagacctcaa gcatgtcaaa tcaactaact gctctaccac tcaaccacac   1620
cctcgcctgc attgttacta ctactattat tatcttgata caggtctcca cattgagctc   1680
accctcacag tctccacatt gagctcaccc tcacagtctc cacattgagc tcaccctcac   1740
agtctccaca ttgagctcac cctcacagtc tccacattga gctcaccctc acagtctcca   1800
cattgagctc accctgtggc tctggcaaac cttgaattct ctcattcctc ctgcctcagc   1860
ctctggggtc gtggggatta gccaaaccca cttgaggttt tcttcaatca gcaaattctt   1920
agcgttcaat taacacacac tcataactcc agtactttgg aaaccggaac aggagaattt   1980
ctgtgagctg gaggctagct tggactacag tatgagaccc tgtctctaaa taaatacaca   2040
aagaaatctc accaagggcc tccctctctc agcaagctct aactgtggtg ggagttctgg   2100
gttgttccag ttaacgggct cagaactcta ctgcccagca catcagcccc tagacacagg   2160
tggctctcta catgtgaaca tgcagtcaca gaaatgaaat aaagtgaaaa ttttatttct   2220
tcagttgtat agcctcttcc gtgtgggctg tagttactgt cttgaatagg ataggctcag   2280
aatccttggt gctggaacca agagtttgat tccattagac gacagggaat ataatgccca   2340
atagggcatt cctcctcccg gtcactagcg gtgcactttc tccgaatctt tgtcatgttg   2400
aattagaaaa gttagtattt tcctccatcc cttcccctcc tcccctcctc ccctcctccc   2460
```

-continued

```
ctcctcccct cctccctccg tctccccgcc cctcccctcc ccctctgatc ctcccccatc   2520
tatcaaatcc aagaattcca gtaaaaagag gaaaacaatc gaagtgattt cgttgattgt   2580
cagttccacc aaagcaagac ttgactttag ttccgcgttt cggttcccgg catgcaccac   2640
agccagcgag caccgtggaa ggatgctagc acggtcctcc ccccgccccc actagctgtc   2700
ttcagctccc cagtagaggg caaccgcact ccagattctc aatggagagt gtttacacaa   2760
tcgttgcggg tttgtgtgag cgcgcccgct tccagagaca cttcttcttt ttcttttttc   2820
catttcatcc cagtggcaac gcagagtgcc agatcattca ggccgtttgc agggcaagcc   2880
gtgggagctt ggcaagcaag gccccatttc ctagggaacc cgtgcctggc gcttcaggaa   2940
agcacgggaa cctggcactg tgactctgcg ggtattattt tgcagaactc tttattaaac   3000
gggagtttca agtccagctg gagacgacca ggcagcgcct ttaaccccag agtcacacac   3060
aggtgccttt tcttggggcc agattggggt tgtgtggcag acctgcgacc agcttgacaa   3120
ctcttctgcc aggccacaaa atggtgttgg ctgtaagagg tgacaccagg gacagggaag   3180
atcgctgcta ttctcctgag ctctccaaag acccacacca gtctgtcccc ctttcctcct   3240
gctcttcccc tgtatcgccc cctcaccatc tcccccaacg agactcttgg catctcctcg   3300
gcacaaggat ttgaaaatag atgcttgggg gtgagaagaa gaagagagaa agagagagaa   3360
ggaaggaagg atatatagat gatacagacg catacaggtg acatgtagct aatcattttt   3420
aattaaaaaa taaattaaaa gcaaatcaag gatatatatg atacccttag agcaagtgtc   3480
tcatacacac acaaacacac acacacaata tatatatata tatatatata tatatatata   3540
tatatatata ttatacttgg aacaagtgtc cagaagggct ggggactcta aagtgcttgt   3600
caaagccagg ctcacatcag taatcttatc acctggtaga ctgagacagg aggattttga   3660
tgagttcagg cccagcctga gctgcagaat gtgattctat cccaaaaaag taaaataaaa   3720
taaaattcaa aatacacgaa aagagtattt gctgaacaaa caagcctaaa gccctggatc   3780
ccttccccca tgtcctaaga aaataagttt cttgaagctg gagggatggc tcagaggtta   3840
agagccccag ctgcacttgc ggaacactaa gacccagttc ccagacccca cactgtgggt   3900
cacaactgtc tcaaacgcca gctccggagg atccatgccc tctcctggcc tccaccggca   3960
ccaagaacac atacagtgcc catacattta tgcaagcaag gtattcacgc acataaaact   4020
aaaagaatat ttaataaaga tataacaaaa tagcatgaag cccagctggt acagaggttc   4080
aaactacatc ccaggttcat ccctctgcct ttgctctcag ttggcttggg taggtctctt   4140
ctctgaactg gcgccctgcg ggttccacat tgagaccctc tcatttttaa acctacttct   4200
tctgggcggg gttaattgct gccagggctc aagccaacgc ttcctcttct ccacagcaat   4260
cttccaagtt tcacgagata accaggaact gctaagttca tgtgaacctt agtgaagaac   4320
ctgagtcttc ccatgtgatt ggtgtgtgca tgtgtgcata cacaaatgta tgtgtgtgct   4380
ctatgtgtgc ctatgtatgt gtgcatgcat gtgtgcatat acaaatgcat atatgtctat   4440
gtagtgtgcg tacacaaatg tatgtgtgtg ctcaatgtgt gcctatgtgt gtgtatgcat   4500
gtgtgcgtac acaatgcatg tgtgtggtgt ctgtgtgcct gtgtgtgtat gcatgtatgc   4560
atacacaaat gtatatgtgt ggtgtgtgaa tgtgtgccta tgtatgtgtg tgctgtgtgt   4620
gggtgtggta tgtgtgtgat gtgtggaggg gtgtgtatgt gtggtatgta taggtgatac   4680
gtttggggtg taatatgcgt atgtggtttg tgaaatgtag ttcgtgtgtg tgcatgtgtg   4740
cgtgcgtgcg tgcgtgcgtg cgtgtgtgtg tgtgtgtgtg tgtgtgtgtt ggatatagta   4800
tgtgtgaggt gtgtgtactc accatggcct ccctcacttg ggggagtgaa gtcagcagcc   4860
```

tggaccactc agggacatga gatactcaga cacatcttga tttccacccc tcttttcctg 4920
atcctccttc acgtgtcact ttcccaaaca ctggacaaca gtttgggggc atctgattcc 4980
actaatgaca gggacatcac atgtctccag agggaacacc ttctgtgtca catgtcatct 5040
gagaatgtag cagagtcaca gagaaatgtc acagaaacca aaatgcagag taccaaggta 5100
tagctaggca cagagcagag gggaagccgc tgaatttatt aaaaatgtca gaatcgtaaa 5160
agacagggga cagcggtggg gacattcagg gtccagtagc acacaggcag tccaaacctg 5220
atcactggaa ggtagtaggt aaggaaaggc tgcacacaga ttattcacac agtttataca 5280
tgtacacaga ttattcacat ggtttgtgta tgtgcacaga ttattcacac agtttataca 5340
tgtgtggctt cgtggtaact ttgagcttac tttcaattta aaaggatctc tctcacaagc 5400
tggggccggg aatggctgca gtcaacactc catcacttag tcacactgtg caaacagcac 5460
ctcctgactc atggtgactt gtagtaaaat gaagaggcca catttgcatc caagacagct 5520
catcagtacc tagtgaagaa tctgtccctg agtatttgca tgaatggacc cgggtccagg 5580
gcctggctgg gagtctccag gtgttgcagc cagaatgtca ttgtgttttt tcaggatccc 5640
agaagtttct aaaatacagg ccaagtactc atttgtgtta caaagtatct gactaataga 5700
agtgattagg taacacaaag ccttttaaaa accgagatca cccttgtcat gtccctggcc 5760
tcttagaaca agatccaagc ttttgctggt tgacaagtgg ggccatccag tgcgtctccg 5820
ttcctgctac ttcatctgga agacctctcc cactaacttg cccctgaccc ctcacacctg 5880
ctgtttcctt tccacccgga agtgcttgtc taggctttca tggccatctg actgagcatc 5940
taggcctcag tccagtggtc cctcagctct ctctagtcac tgtactaatg gaaacggcca 6000
ctaactacat tttcaatatg gaagcctcct cctcaggaac ctccaagggc agaagcctcc 6060
agagaaccac tcctgacccc ctggagttct gagtgcttct ggccctctct gtgtctgcag 6120
gactattcac cacttgtgtt gaatggttca gtcctcacct cctctggcat gtgctcagtt 6180
ctcatctcat tggggagtcc ttcccaggtc actcttctct cctgtctttg aagtgttttt 6240
ttccttcatg gtatttctgt ctgggcacac acacagacac acatacacac acatacacac 6300
ccatgcagta tggcagatac atcacctatg tttcagattt ttattctacc atcacccaat 6360
acctgaatcc ccgaaaaagc cttagaaagc caggaatttg tgtatttttg tcagcactcc 6420
accccagcac ctgaagccaa gcctgactta atatttttgg ttttgtttct aga 6473

<210> SEQ ID NO 4
<211> LENGTH: 7045
<212> TYPE: DNA
<213> ORGANISM: Cricetulus griseus

<400> SEQUENCE: 4
caattgatta tagatggatg atagatagat agatagatag atagatagat agatagatga 60
tggatagaca gatgatggat agttagagga tagataatga ctgaataata agtacataaa 120
tagatgatag agcggggcgt tggtggtgca cgtctttaac cccagcacca gagaggcaga 180
ggcagttgga tctctgtgag tttgaggaca gcctggttac agaatgggtt ccaggacagc 240
caaggctgtc actcagagaa atactgtctc aaataaaaaa agtaagtaaa caaataaata 300
aatgataact agttagaaga tagatgattg aatgataggt agataaatag aagatagata 360
gatagatgat tgatagatga tagacagata gacagacaga cagacagaca gacagcagaa 420
agataatgca cggtgaaaca tggtctgatt tagttagcaa gatcagagaa gccttctttg 480

-continued

```
aaagtgacat ttgagagcat ttcaaacgct gttcatgtca ggcatgccaa tggggagaga    540
agggcttgca gaaagcaggc ccggcaagcc atggggagca agctaggagg cagcattcct    600
tgcatttgcc tctgcctcag ctgcttcctg gagttccccg gtttttatca caacagtaga    660
aataaaacca ggacaatgtt gtttccatgc atacatctgc aagaacttac tccggttcaa    720
tagacagacc aaggcacctg tgtttgctca agaagcacgg agggaggtgt gtgcacctgc    780
tgggtgctgg tgctctggct gtgccagaca gagagcaaga caggaaagtt cctggtggcc    840
tagagcacac agcccagccc aggaagtcat gtctctctct gtctctgtct ctgccccacc    900
cccaccccat ttaggccaga gaacagctgt ggcaagcttt gggtttgggt gagtcattcc    960
tcaagagcca agagccgccc accttgtatg gggtagtttg ttgttgttgt tgttgttatt   1020
atttgtttgt ttgtttgttt ggtaaaggtt tttcaatagg agttggaatt tggcaattca   1080
gctaggctgg ctgagcagcc agctagcccc gggcactcat ccgtctctac ctccccagtt   1140
ctgggatttc gggtacatgc tgccacatcc gactttttc ccctgctcca gttcttaaga   1200
ccaagtcttc atgtcaaaca cttcaccacc ttagccatct ttctgggtca gaagttagat   1260
cttcaggaag acaaggagtg tatcaggaca tgagcgtgcc ccaactctgc tcagaccttc   1320
tgatagagaa aatgggggga ggggtgtcag aggctgccgg agaaagacaa gtccaggtta   1380
aggaggacga ccctgggctc tgaatccaag ggtgattccc tcaccttgta cacttggcat   1440
tttgggaagg aagcatcaga taaaagcagt gcagacatag tcaggaatat ttacacgtgt   1500
gagtcaacct gggagtgagt ctgtgtacaa ctgaacatga agcaagtttt gaagcttcat   1560
ttccagacta ttcccagggt gcaataactt cctgttttcg ttgcagcctt cccagtctct   1620
gccactgcca tctctacttc agtctggaat ggtgggcaca cagaaaaagt ctatggcaat   1680
cctgcgagaa gacaagtggg cgcctgactt cgggctcctg ttacaagaga ggaatccagg   1740
agtttatttt gcagctgatt cagtgttgac caagagtcca gctctggggg agtgggaagc   1800
aaccaaagca gagacaggtc ccagcacaat tttggtttt caagacagca cttctctgtg   1860
gctttgaagg ctatcctaga actgttcttt gtatatcctt ccttgcaact agctcttata   1920
gaccaggctg gtcttgaact cacagagatc catctgcctc tgcctcccaa gtgctgggat   1980
taaaggcgtg cacctcggct gccaccaccc agctacatac ataatttaca ataataaaaa   2040
taaaatactt taaagtgtta tagcagtttg aatgtaattg gccctgtcat ctcataggga   2100
gtggcactat taggaggtat ggctttgttg aaggaaatat gtcactgtga gggtgggctg   2160
tgaggtttcc tatgctcagg gtaccagcca gtgtctcagc tgaggtcctg ttgcctgcaa   2220
gatgtaggac tctcatccct ttctccagca ccatgtctgt ctgcatgcca tcatgttccc   2280
agccatgatg acaatgtact aaaacctctg aaactgccac ccaactaaat gttttccttt   2340
ataagagttg ccatgctcat ggtgtctctt cacagcaata gaaaccctaa ctaagataag   2400
tgtattctcc cctactcccc atgatttaaa atttaggaag gcaggtaggc aggcaggcag   2460
gctggtatag tggttcattc tagcacctga gacctggaat gggaggattg tgagttagtt   2520
ctaggccatt ctggtgccta gaaaccagag ccgggggttg gcccaatgca gagcacttgc   2580
tctacgtatg gcccagcaca ataagtcaat ttcctcacct taaaggcttg acaatttaaa   2640
aacactggtt tttagttagt ccgtgtctgc tccacagatg gagacagcta atcacagatg   2700
catcaggggc cttcctgagt gctaaacatc aaacagcctt ctcccctcct gagcctttgt   2760
gtgcagaatg tgtccatcgc aagaagcaaa cagtcttgct tgcccaccaa cttccttcct   2820
gcatcagaag agctgggtgc aaactgcaag agtagcctca ccttagagat gggtcccatt   2880
```

-continued

```
gctctacatg ggagcattac cttccaagaa ggcaaaaatg tctcctggtt gagctttttt   2940
tgtcacctgt taaaggcaaa tcaacagaga ggctttgtct cacccactaa catcttggaa   3000
acaaatacca acgaacgctg gggaggatgt ggggaaagca gagccctcat gctctccgag   3060
ggaaaatcac acccactgtg gaacagtgtg gaaacctcaa agactgggat tacaagcagc   3120
acacaagcca gccacgctac tcctggtcac acaccacaaa gacgcttgca cattcacgct   3180
tacgctgcga acactagcaa cgttcccact gcctcctttg agccccgccc cccgcccctg   3240
ccccccgccc cgcccctgtg gtctatgttc ctcttcccta aagtcagctt ccacttctct   3300
gtctccatct tcgccccacc ctccctcctc gctacataat tgtctctatt ccatttctct   3360
gctttgaaac agctttttgc aaagcatcaa atctattgtc ctatgcccca aatcaacctc   3420
cagtttcaca agtgatacag gaaatcgttt tcctaattaa aaatcccccc tttgaccatt   3480
tattcccact cttggaacat cttccccttg aggaaagtta cagaatgagg tggctctcct   3540
cttcctattc gaggtgtttc cttcagactt tgtccgtgtc taatcttttt aactgttggc   3600
caggcctcca ccacggcaca gatgaactgt ggggttcatt tacctgaaac tctatggaag   3660
gatgtttatt tctccttcac tttagcaaat gataaagggc accattcact ctgtctattc   3720
tgcaggggcc attcctttct ctaggccaga tactgagaat tgctcccaga atcaatgtgg   3780
tatacatatt tccccttcaa cattgatagg cattgatcac acacacacac acacacacac   3840
acacacacac acacagtagc acaaatgtat tcccctagcc cgcttccatc ttgccacagg   3900
actccagagt ggccctggat agcaagcttc ctgttttgtt tctctgttcc tgctgctttt   3960
ccaccctcca gtctatcttt tctaagtcct tctgccattg tcctcttccc aactgtcctg   4020
agatgcagtc attgtctggg attcagacct tctctctctg cccaagtgag tatattgacc   4080
cccacggttt gtacaaccat aacttcaggg agcccgacaa aaactgtttt atgagccaag   4140
tagtcccagg acttgagagg tagaggcggg aagatcagca gtttgaggcc agcctggaga   4200
gcataagagc cggtctcaaa acaacaatgg aaactagata ctaagtaaaa atcctggggt   4260
gtttcatcat gaatgtctgt tcttctagta ccacgctgaa ctccgtacac agctccagct   4320
gttacggctt tcttagaatc catactcttt tttttttttt tttttttttt ttttttttgg   4380
tttttcgaga cagggtttct ctgtggcttt ggaggctgtc ctggaactag ctcttataga   4440
ccaggctggt ctcgaactca cagagatcca cctgcctctg cctccagagt gctgggatta   4500
aaggcgtgcg ccaccaacac ccggcagaat ccatactctt tttaaaaaaa gatttatcaa   4560
tttactatgt atacagcttt ctgcctgcat gtatccatgc atgtcagaag atggcaccag   4620
gtcgcattac agatggttgt gagccaccat gtggttgctg ggaattgaac tcagaatgtc   4680
tagaagagca accagttctc ttaacctctg agccatctct ccggccccca gaaatccata   4740
ttcttgagga ttttttacac cccccccacc aaaagacgta tatctaaatt ttaatgtgag   4800
aattcacatt ttcttaagag ttgaacatag atttagagga aaatcagatc ccacatgatt   4860
aacaaagcat gcttgtgggc aggtctgcta ccaagaggtg ggccgtagct tctagctcag   4920
acaaactcac tcccttcctc gtggcctctt cgccctcaag tcagaaactc accctgtgat   4980
tctgccccag aagttgctct agagcacagt gcatccttcc gtcttcactc tgtggcttga   5040
attgtgtcca tcgcttatga ttacaacccc tcacagagca tcctaactgg tttctttgca   5100
tgcctatggg cactcctcca ttctagaaca cccttgccat caatactatg aaaggagggg   5160
tggaggagga agagcaggaa gaggaggggg aagcgaggga agaggaagac acggatggca   5220
```

-continued

```
atgaggaggg gggagcaccc aagtcctccc tggatgagag tctcactggg agacttaata   5280

ttaattataa atgcttggtc agcagctggg caggataagg ttaggcagga gaaccagact   5340

aaggactctg ggaagcagaa gggcagagtc agacaaggag aggaaacagg aagtacaagg   5400

taaagtcacg tggcagaatg tagataatag aaatgggttc atttaagttg gaagagttag   5460

ctagtaacaa gcctgagcta tcagccgagc atttataatt aatattgagc ctccatattg   5520

gttatctggg aattggcggg cagaaaaaaa aaagtctgcc tacaagtcaa tgtcatgtag   5580

ctcccaaagc caaggtacct ttgttcagtg cttgactgag ccagcattat aaattttctc   5640

cagatgtacc gaatcacatt tcatagcaac atgcagacat caagttttcc ctgaagctct   5700

aaccagctgg ttgcatgctg tccggagtct cagctataac ccagaagtga cctgggtcgg   5760

ggaagaggtg gtactttgcc ttctttgcac tctctgtgtt gcctcaccca ttcagcttca   5820

agcaatgtga ctgcctgacc ctgagggcgt ttacaacgcc tgacccacag accacaagtc   5880

aaccagctgg tgtgctcacg atacctagtc tgaaccatag ccctgctccc accctgcctc   5940

catctccacc ctttcttcac tgctcatcac agctggctag caaagactgc ctcagacctg   6000

agcacaggct ccactccaca gccgtgactg ttcgagccac ttaaatcaaa gagcgcttgt   6060

cttccgctca gtaaatctct cctcagctca ctgatgacgt tgactttctc tagacagcac   6120

atttgggttt aagacactgc tacttgagct cttcattcag ttcctcagaa tacctcattt   6180

gggtcagatt cccaaagagg aagatagggt tcctggcaga cagacatgtc tcattccttt   6240

gaaatccttc agagaaatgc agtgactatg gcaccttctt aaaaagcaca cacacaaata   6300

acacacacac acacacacac acacacacac acacacacac atatccccct cactgtcatc   6360

cttgatatgt atatgatata tataaaatca ttgttttata ctgtgataat tgattatgaa   6420

taaaatttac taaaatgaac aattaaaatt atgggggggg ctggagagat ggctcatcag   6480

ttaagagaac agttgctgct cttgcagaac acgagagttc agttcccagc acccacatca   6540

ggcagctcat aaccatgtgt ggtgtcagtt ccaggagatc tggtgccctc ttctggcctc   6600

ctccagcacc tgctacatgt ggttcacaca cacacacaca cacacacaca cacacacaca   6660

cacacacaca caaataaata taaagattat tttttcaaa actgagttaa aaataggttc   6720

tatctgattc atactaaggc ttttcacagt ggttaagtct attagatatg tctagccata   6780

tcctttctcc cttctttctt gaggagaggc ttttaaagct acaagttaca gccttctttg   6840

caaataagag taccatttaa caggcctctg accaatgaga tgccagaatc ggttgcccag   6900

gagcttccca aacagtccat tatagggaaa ggtggtacaa accagtagat taggcatgtt   6960

ccacttccta agtgccgtgc caaataagga aatggcctca aatgtttgcc ttttatcttc   7020

acccacctct gaattgcacg ctagt                                         7045
```

<210> SEQ ID NO 5
<211> LENGTH: 13515
<212> TYPE: DNA
<213> ORGANISM: Cricetulus griseus

<400> SEQUENCE: 5

```
tctagaaaca aaaccaaaaa tattaagtca ggcttggctt caggtgctgg ggtggagtgc     60

tgacaaaaat acacaaattc ctggctttct aaggcttttt cggggattca ggtattgggt    120

gatggtagaa taaaaatctg aaacataggt gatgtatctg ccatactgca tgggtgtgta    180

tgtgtgtgta tgtgtgtctg tgtgtgtgcc cagacagaaa taccatgaag gaaaaaaaca    240

cttcaaagac aggagagaag agtgacctgg gaaggactcc ccaatgagat gagaactgag    300
```

-continued

```
cacatgccag aggaggtgag gactgaacca ttcaacacaa gtggtgaata gtcctgcaga    360
cacagagagg gccagaagca ctcagaactc caggggggtca ggagtggttc tctggaggct    420
tctgcccttg gaggttcctg aggaggaggc ttccatattg aaaatgtagt tagtggccgt    480
ttccattagt acagtgacta gagagagctg agggaccact ggactgaggc ctagatgctc    540
agtcagatgg ccatgaaagc ctagacaagc acttccgggt ggaaaggaaa cagcaggtgt    600
gaggggtcag gggcaagtta gtgggagagg tcttccagat gaagtagcag gaacggagac    660
gcactggatg gccccacttg tcaaccagca aaagcttgga tcttgttcta agaggccagg    720
gacatgacaa gggtgatctc ggtttttaaa aggctttgtg ttacctaatc acttctatta    780
gtcagatact ttgtaacaca aatgagtact tggcctgtat tttagaaact tctgggatcc    840
tgaaaaaaca caatgacatt ctggctgcaa cacctggaga ctcccagcca ggccctggac    900
ccgggtccat tcatgcaaat actcagggac agattcttca ctaggtactg atgagctgtc    960
ttggatgcaa atgtggcctc ttcattttac tacaagtcac catgagtcag gaggtgctgt   1020
ttgcacagtg tgactaagtg atggagtgtt gactgcagcc attcccggcc ccagcttgtg   1080
agagagatcc ttttaaattg aaagtaagct caaagttacc acgaagccac acatgtataa   1140
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtccccaccg ctgtcccctg tcttttacga   1320
ttctgacatt tttaataaat tcagcggctt cccctctgct ctgtgcctag ctataccttg   1380
gtactctgca ttttggtttc tgtgacattt ctctgtgact ctgctacatt ctcagatgac   1440
atgtgacaca gaaggtgttc cctctggaga catgtgatgt ccctgtcatt agtggaatca   1500
gatgccccca aactgttgtc cagtgtttgg gaaagtgaca cgtgaaggag gatcaggaaa   1560
agaggggtgg aaatcaagat gtgtctgagt atctcatgtc cctgagtggt ccaggctgct   1620
gacttcactc ccccaagtga gggaggccat ggtgagtaca cacacctcac acatactata   1680
tccaacacac acacacacac acacacacac acgcacgcac gcacgcacgc acgcacacat   1740
gcacacacac gaactacatt tcacaaacca catacgcata ttacacccca aacgtatcac   1800
ctatacatac cacacataca cacccctcca cacatcacac acataccaca cccacacaca   1860
gcacacacat acataggcac acattcacac accacacata tacatttgtg tatgcataca   1920
tgcatacaca cacaggcaca cagacaccac acacatgcat tgtgtacgca cacatgcata   1980
cacacacata ggcacacatt gagcacacac atacatttgt gtacgcacac tacatagaca   2040
tatatgcatt tgtatatgca cacatgcatg cacacataca taggcacaca tagagcacac   2100
acatacattt gtgtatgcac acatgcacac accaatcaca tgggaagact caggttcttc   2160
actaaggttc acatgaactt agcagttcct ggttatctcg tgaaacttgg aagattgctg   2220
tggagaagag gaagcgttgg cttgagccct ggcagcaatt aaccccgccc agaagaagta   2280
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctattttgtt atatctttat taaatattct tttagtttta   2460
tgtgcgtgaa taccttgctt gcataaatgt atgggcactg tatgtgttct tggtgccggt   2520
ggaggccagg agagggcatg gatcctccgg agctggcgtt tgagacagtt gtgacccaca   2580
gtgtggggtc tgggaactgg gtcttagtgt tccgcaagtg cagctggggc tcttaacctc   2640
```

-continued

```
tgagccatcc ctccagcttc aagaaactta ttttcttagg acatggggga agggatccag   2700
ggctttaggc ttgtttgttc agcaaatact cttttcgtgt attttgaatt ttattttatt   2760
ttactttttt gggatagaat cacattctgc agctcaggct gggcctgaac tcatcaaaat   2820
cctcctgtct cagtctacca ggtgataaga ttactgatgt gagcctggct ttgacaagca   2880
ctttagagtc cccagccctt ctggacactt gttccaagta taatatatat atatatatat   2940
atatatatat atatatatat atatattgtg tgtgtgtgtt tgtgtgtgta tgagacactt   3000
gctctaaggg tatcatatat atccttgatt tgcttttaat ttattttttta attaaaaatg   3060
attagctaca tgtcacctgt atgcgtctgt atcatctata tatccttcct tccttctctc   3120
tctttctctc ttcttcttct cacccccaag catctatttt caaatccttg tgccgaggag   3180
atgccaagag tctcgttggg ggagatggtg agggggcgat acaggggaag agcaggagga   3240
aagggggaca gactggtgtg ggtctttgga gagctcagga gaatagcagc gatcttccct   3300
gtccctggtg tcacctctta cagccaacac catttgtgg cctggcagaa gagttgtcaa   3360
gctggtcgca ggtctgccac acaaccccaa tctggcccca agaaaaggca cctgtgtgtg   3420
actctggggt taaaggcgct gcctggtcgt ctccagctgg acttgaaact cccgtttaat   3480
aaagagttct gcaaaataat acccgcagag tcacagtgcc aggttcccgt gctttcctga   3540
agcgccaggc acgggttccc taggaaatgg ggccttgctt gccaagctcc cacggcttgc   3600
cctgcaaacg gcctgaatga tctggcactc tgcgttgcca ctgggatgaa atggaaaaaa   3660
gaaaaagaag aagtgtctct ggaagcgggc gcgctcacac aaacccgcaa cgattgtgta   3720
aacactctcc attgagaatc tggagtgcgg ttgccctcta ctggggagct gaagacagct   3780
agtgggggcg gggggaggac cgtgctagca tccttccacg gtgctcgctg gctgtggtgc   3840
atgccgggaa ccgaaacgcg gaactaaagt caagtcttgc tttggtggaa ctgacaatca   3900
acgaaatcac ttcgattgtt ttcctctttt tactggaatt cttggatttg atagatgggg   3960
gaggatcaga gggggagggg aggggcgggg agacggaggg aggaggggag gaggggagga   4020
ggggaggagg ggaggagggg aagggatgga ggaaaatact aacttttcta attcaacatg   4080
acaaagattc ggagaaagtg caccgctagt gaccgggagg aggaatgccc tattgggcat   4140
tatattccct gtcgtctaat ggaatcaaac tcttggttcc agcaccaagg attctgagcc   4200
tatcctattc aagacagtaa ctacagccca cacggaagag gctatacaac tgaagaaata   4260
aaattttcac tttatttcat ttctgtgact gcatgttcac atgtagagag ccacctgtgt   4320
ctaggggctg atgtgctggg cagtagagtt ctgagcccgt taactggaac aacccagaac   4380
tcccaccaca gttagagctt gctgagagag ggaggccctt ggtgagattt ctttgtgtat   4440
ttatttagag acagggtctc atactgtagt ccaagctagc ctccagctca cagaaattct   4500
cctgttccgg tttccaaagt actggagtta tgagtgtgtg ttaattgaac gctaagaatt   4560
tgctgattga agaaaacctc aagtgggttt ggctaatccc cacgacccca gaggctgagg   4620
caggaggaat gagagaattc aaggtttgcc agagccacag ggtgagctca atgtggagac   4680
tgtgagggtg agctcaatgt ggagactgtg agggtgagct caatgtggag actgtgaggg   4740
tgagctcaat gtggagactg tgagggtgag ctcaatgtgg agactgtgag ggtgagctca   4800
atgtggagac ctgtatcaag ataataatag tagtagtaac aatgcaggcg agggtgtggt   4860
tgagtggtag agcagttagt tgatttgaca tgcttgaggt ctcccggtcc atctgtggcc   4920
ctgcaacagg aagggaggga ggaagggggg gaacgagaga gaggaaagag agacagaagc   4980
taagataggg aatgagagag gaaggaagaa acgggaagaa attcagactc cttcctgagt   5040
```

-continued

```
tccgccaacg cctagtgaca tcctgtgcac accctaaggt ggcctttgtg tggcactggc   5100
ttgggtggtc gggaaaggca ttttcagctt gttgcagaac tgccacagta gcatgctggg   5160
tccgtgaaag tttctgcccg ttaacaagaa gtctctacta cttgtgacct caccagtgaa   5220
aatttcttta attgtctcct ggtgttctgg gttttgcatt tttgtttcta aggatacatt   5280
cctgggtgat gtcatgaagt ccccaaagac acagtggggc tgtgttggat tgggaaagat   5340
gatttatctg ggtgtcaaa aggaaaagaa gggaaacagg cacttgggaa aatgtcctcc   5400
cgcccacccg aattttggct tggcaaccgt ggtggaggag caagaaacac gtggacgttt   5460
gaggaggcat ggggtcctag gaggacagga agcagaagga gagagctggg ctgacagcct   5520
gcaggcattg cacagtttca gaaggagatt acagcatgac tgagttttta gggatccaac   5580
agggacctgg gtagagattc tgtgggctct gaggcaactt gacctcagcc agatggtatt   5640
tgaataacct gctcttagag ggaaaacaga catagcaaac agagccacgt ttagtgatga   5700
aactctcact ttgcctgagt catgtgcggc catgcccagg ggtcaggctg acactcaact   5760
caaaaacaag tgagaaattg aagacaatcc gtggtggcag ctactggaag ggccaccaca   5820
tccccagaaa gagtggagct gctaaaaagc catttgtgat aggcacagtt atcttgaatg   5880
catggagcag agattacgga aaaatcgaga atgttaatga ggcaacattc gagttgagtc   5940
attcagtgtg ggaaacccag acgcttccat cccctaaaag gaacatcttg ctctcagtca   6000
aaatggaaat aaaaattggg gcttgaattt ggcaaatgat tcagaactct gtgtaggtat   6060
tttcacacgc acagtggata attttcatgt tggagtttat ttgtgctaaa aggcagaaaa   6120
gggtaaaaag cacatcttaa gagttatgag gttctacgaa taaaaataat gttacttaca   6180
gctattcctt aattagtacc cccttccacc tgtggtaatt tcctgagata gtcagtgggg   6240
aaaagatctc tccttctctt ctttctcccc ctcccctcct ctccctccct ccctccctcc   6300
ctccctcctc tccctccctc cccctttcct tctttctttg ctccttctcc tctgcctcct   6360
tctccctttc ttcttcattt attctaagta gcttttaaca gcacaccaat tacctgtgta   6420
taacgggaaa acacaggctc aagcagctta gagaagattg atctgtgttc actagcgtgc   6480
aattcagagg tgggtgaaga taaaaggcaa acatttgagg ccatttcctt atttggcacg   6540
gcacttagga agtggaacat gcctaatcta ctggtttgta ccacctttcc ctataatgga   6600
ctgtttggga agctcctggg caaccgattc tggcatctca ttggtcagag gcctgttaaa   6660
tggtactctt atttgcaaag aaggctgtaa cttgtagctt taaaagcctc tcctcaagaa   6720
agaagggaga aaggatatgg ctagacatat ctaatagact taaccactgt gaaaagcctt   6780
agtatgaatc agatagaacc tatttttaac tcagttttga aaaaaataat ctttatattt   6840
atttgtgtgt gtgtgtgtgt gtgtgtgtgt gtgtgtgtgt gtgtgtgtgt gaaccacatg   6900
tagcaggtgc tggaggaggc cagaagaggg caccagatct cctggaactg acaccacaca   6960
tggttatgag ctgcctgatg tgggtgctgg gaactgaact ctcgtgttct gcaagagcag   7020
caactgttct cttaactgat gagccatctc tccagccccc cccataattt taattgttca   7080
ttttagtaaa ttttattcat aatcaattat cacagtataa aacaatgatt ttatatatat   7140
catatacata tcaaggatga cagtgagggg gatatgtgtg tgtgtgtgtg tgtgtgtgtg   7200
tgtgtgtgtg tgtgttattt gtgtgtgtgc tttttaagaa ggtgccatag tcactgcatt   7260
tctctgaagg atttcaaagg aatgagacat gtctgtctgc caggaaccct atcttcctct   7320
ttgggaatct gacccaaatg aggtattctg aggaactgaa tgaagagctc aagtagcagt   7380
```

-continued

```
gtcttaaacc caaatgtgct gtctagagaa agtcaacgtc atcagtgagc tgaggagaga   7440
tttactgagc ggaagacaag cgctctttga tttaagtggc tcgaacagtc acggctgtgg   7500
agtggagcct gtgctcaggt ctgaggcagt ctttgctagc cagctgtgat gagcagtgaa   7560
gaaagggtgg agatggaggc agggtgggag cagggctatg gttcagacta ggtatcgtga   7620
gcacaccagc tggttgactt gtggtctgtg ggtcaggcgt tgtaaacgcc ctcagggtca   7680
ggcagtcaca ttgcttgaag ctgaatgggt gaggcaacac agagagtgca aagaaggcaa   7740
agtaccacct cttccccgac ccaggtcact tctgggttat agctgagact ccggacagca   7800
tgcaaccagc tggttagagc ttcagggaaa acttgatgtc tgcatgttgc tatgaaatgt   7860
gattcggtac atctggagaa aatttataat gctggctcag tcaagcactg aacaaaggta   7920
ccttggcttt gggagctaca tgacattgac ttgtaggcag acttttttt ttctgcccgc   7980
caattcccag ataaccaata tggaggctca atattaatta taaatgctcg gctgatagct   8040
caggcttgtt actagctaac tcttccaact taaatgaacc catttctatt atctacattc   8100
tgccacgtga ctttaccttg tacttcctgt ttcctctcct tgtctgactc tgcccttctg   8160
cttcccagag tccttagtct ggttctcctg cctaacctta tcctgcccag ctgctgacca   8220
agcatttata attaatatta agtctcccag tgagactctc atccagggag gacttgggtg   8280
ctccccctc ctcattgcca tccgtgtctt cctcttccct cgcttccccc tcctcttcct   8340
gctcttcctc ctccacccct cctttcatag tattgatggc aagggtgttc tagaatggag   8400
gagtgcccat aggcatgcaa agaaaccagt taggatgctc tgtgaggggt tgtaatcata   8460
agcgatggac acaattcaag ccacagagtg aagacggaag gatgcactgt gctctagagc   8520
aacttctggg gcagaatcac agggtgagtt tctgacttga gggcgaagag gccacgagga   8580
agggagtgag tttgtctgag ctagaagcta cggcccacct cttggtagca gacctgccca   8640
caagcatgct ttgttaatca tgtgggatct gattttcctc taaatctatg ttcaactctt   8700
aagaaaatgt gaattctcac attaaaattt agatatacgt cttttggtgg gggggtgta   8760
aaaaatcctc aagaatatgg atttctgggg gccggagaga tggctcagag gttaagagaa   8820
ctggttgctc ttctagacat tctgagttca attcccagca accacatggt ggctcacaac   8880
catctgtaat gcgacctggt gccatcttct gacatgcatg gatacatgca ggcagaaagc   8940
tgtatacata gtaaattgat aaatcttttt ttaaaaagag tatggattct gccgggtgtt   9000
ggtggcgcac gcctttaatc ccagcactct ggaggcagag gcaggtggat ctctgtgagt   9060
tcgagaccag cctggtctat aagagctagt tccaggacag cctccaaagc cacagagaaa   9120
ccctgtctcg aaaaaccaaa aaaaaaaaaa aaaaaaaaaa aaaaaaaaga gtatggattc   9180
taagaaagcc gtaacagctg gagctgtgta cggagttcag cgtggtacta gaagaacaga   9240
cattcatgat gaaacacccc aggattttta cttagtatct agtttccatt gttgttttga   9300
gaccggctct tatgctctcc aggctggcct caaactgctg atcttcccgc ctctacctct   9360
caagtcctgg gactacttgg ctcataaaac agtttttgtc gggctccctg aagttatggt   9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa aacaggaagc ttgctatcca   9600
gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
```

```
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaaggggg gatttttaat taggaaaacg atttcctgta  10080
tcacttgtga aactggaggt tgatttgggg cataggacaa tagatttgat gctttgcaaa  10140
aagctgtttc aaagcagaga aatggaatag agacaattat gtagcgagga gggagggtgg  10200
ggcgaagatg gagacagaga agtggaagct gactttaggg aagaggaaca tagaccacag  10260
gggcggggcg gggggcaggg gcggggggcg gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttccacac tgttccacag  10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgtttttaa attgtcaagc ctttaaggtg aggaaattga cttattgtgc  10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaattttaa atcatgggga  11100
gtaggggaga atacacttat cttagttagg gtttctattg ctgtgaagag acaccatgag  11160
catggcaact cttataaagg aaaacattta gttgggtggc agtttcagag gttttagtac  11220
attgtcatca tggctgggaa catgatggca tgcagacaga catggtgctg gagaaaggga  11280
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460
ctttaaagta ttttattttt attattgtaa attatgtatg tagctgggtg gtggcagccg  11520
aggtgcacgc ctttaatccc agcacttggg aggcagaggc agatggatct ctgtgagttc  11580
aagaccagcc tggtctataa gagctagttg caaggaagga tatacaaaga acagttctag  11640
gatagccttc aaagccacag agaagtgctg tcttgaaaac caaaaattgt gctgggacct  11700
gtctctgctt tggttgcttc ccactccccc agagctggac tcttggtcaa cactgaatca  11760
gctgcaaaat aaactcctgg attcctctct tgtaacagga gcccgaagtc aggcgcccac  11820
ttgtcttctc gcaggattgc catagacttt ttctgtgtgc ccaccattcc agactgaagt  11880
agagatggca gtggcagaga ctgggaaggc tgcaacgaaa acaggaagtt attgcaccct  11940
gggaatagtc tggaaatgaa gcttcaaaac ttgcttcatg ttcagttgta cacagactca  12000
ctcccaggtt gactcacacg tgtaaatatt cctgactatg tctgcactgc ttttatctga  12060
tgcttccttc ccaaaatgcc aagtgtacaa ggtgagggaa tcacccttgg attcagagcc  12120
```

-continued

```
cagggtcgtc ctccttaacc tggacttgtc tttctccggc agcctctgac acccctcccc  12180

ccattttctc tatcagaagg tctgagcaga gttggggcac gctcatgtcc tgatacactc  12240

cttgtcttcc tgaagatcta acttctgacc cagaaagatg gctaaggtgg tgaagtgttt  12300

gacatgaaga cttggtctta agaactggag caggggaaaa aagtcggatg tggcagcatg  12360

tacccgaaat cccagaactg gggaggtaga gacggatgag tgcccggggc tagctggctg  12420

ctcagccagc ctagctgaat tgccaaattc caactcctat tgaaaaacct ttaccaaaca  12480

aacaaacaaa caaataataa caacaacaac aacaacaaac taccccatac aaggtgggcg  12540

gctcttggct cttgaggaat gactcaccca aacccaaagc ttgccacagc tgttctctgg  12600

cctaaatggg gtgggggtgg ggcagagaca gagacagaga gagacatgac ttcctgggct  12660

gggctgtgtg ctctaggcca ccaggaactt tcctgtcttg ctctctgtct ggcacagcca  12720

gagcaccagc acccagcagg tgcacacacc tccctccgtg cttcttgagc aaacacaggt  12780

gccttggtct gtctattgaa ccggagtaag ttcttgcaga tgtatgcatg gaaacaacat  12840

tgtcctggtt ttatttctac tgttgtgata aaaaccgggg aactccagga agcagctgag  12900

gcagaggcaa atgcaaggaa tgctgcctcc tagcttgctc cccatggctt gccgggcctg  12960

ctttctgcaa gcccttctct ccccattggc atgcctgaca tgaacagcgt ttgaaatgct  13020

ctcaaatgtc actttcaaag aaggcttctc tgatcttgct aactaaatca gaccatgttt  13080

caccgtgcat tatctttctg ctgtctgtct gtctgtctgt ctgtctatct gtctatcatc  13140

tatcaatcat ctatctatct atcttctatt tatctaccta tcattcaatc atctatcttc  13200

taactagtta tcatttattt atttgtttac ttactttttt tatttgagac agtatttctc  13260

tgagtgacag ccttggctgt cctggaaccc attctgtaac caggctgtcc tcaaactcac  13320

agagatccaa ctgcctctgc ctctctggtg ctggggttaa agacgtgcac caccaacgcc  13380

ccgctctatc atctatttat gtacttatta ttcagtcatt atctatcctc taactatcca  13440

tcatctgtct atccatcatc tatctatcta tctatctatc tatctatcta tctatcatcc  13500

atctataatc aattg                                                   13515
```

<210> SEQ ID NO 6
<211> LENGTH: 14553
<212> TYPE: DNA
<213> ORGANISM: Mus musculus

<400> SEQUENCE: 6

```
cttgaagaac acatgttttc caagagggag cacccatgtt ggaatgacaa tgtagttagt     60

gctcctctcc tgtaggttag tgctcctttg ctataggtaa gtgctcctct cctataggtc    120

agtgctcctc tcctataggt tagtgctcct ctcctatagg ttagtgctcc tctcctacag    180

gttagtgctc ctctgctcta ggttagtcct gctctcctat agtacctaga gagctagggc    240

aaatgggcta ggcccgaagt gcagagacaa acagctatgg aagactgggt aagcacttcc    300

aagctacgaa agagcagtgt gaagggtcag ggcttgtgca gttagtaggg gagatcttcc    360

agttgaagaa acagaagaac tgagagccac tgggtatcat cctcctgcgc catgccttcc    420

tggatactgc catgctccca ccttgatgat aatggaatga acctctgaac ctgtaagcca    480

gccccaatga aatattgttt ttatgagagt tgccttggtc atgctgtctg ttcacagcag    540

taaaacccta aataaggcag aagttggtac cagtattgct gtgatagacc tgaccatgct    600

ttcctttgaa agaatgtgga tttggtgact ttggatttgc aacacagtgg aatgctttaa    660

atggagatta atgggtcatc aattcctagt aggaatatgg aagactttgt tgctgggagt    720
```

-continued

```
atttgaactg tgttgacctg gcctaagaga tttcaaagga gaagaatttc agaatgtggc    780
ataaagacag tttttgtggt attttggtga agaatgtggc tactttttgc ccttgtctga    840
aaagtctgcc tgagactaaa gtgaagagaa tcagattaat tgcattgaca agggaagttt    900
gtggctgcgc tatctggaaa cttacagcca gcctcttgga cctcgggtga cttacgcaaa    960
tactcaggga cagagatgct tgactctgta ctgatgagtt gtcttggatg caaatatggg   1020
ctcttcattt gactacatgt cacgatgagt caggagctgc tctctccaga gtgtgacaaa   1080
gcgaggggat gctgacggta gctgttctag ctttgaaggt aagcctgcac ttatgctaaa   1140
gtcacacata cacgagccgg gtggagaacc tgtctgtgtg gagacacctt tcattacctg   1200
tggcatccag cctctcaagc ttggactgcc tgtgtgctcc tggactctgg aggtcccact   1260
gctctgtcct ctgctgctta tgatactgac attttaaaag aatccagtgg ttccccccctg  1320
tactcggtgt ctacttctac ctggatgttc ctcatttatg ttctgtgaca cttctctgtg   1380
actctgctgc attcctgggt gacatgtgga caccctgtcc ctttgcagac catgatgtca   1440
ctgtcactag tggaatcaga tgccccaagt gttgtcctgt gtttgggaac gtgacaggca   1500
gtacagaagc agaagaggaa gggtgaaaac ggaaatgtca cagcagcatc tgatgtgtgc   1560
ctcagtcacg catgctgctg attggaacta ctcagcatga gagagggcca tggtgaatac   1620
acaaccctat acacactgtg tccatttctc tctctctctt acacagagag agagggagga   1680
gggggagggg gaggcggagg gggaggggga gggagaggga gtgggagagg gagagggaga   1740
gggagaggga gagggagagg gagagggaga gggagagttt aatgtctgtg aagagatacc   1800
atgaccaaag caactcttat aaaggacaac atttaattgg ggctggctta caggttcaga   1860
aattcagtcc attctcacca tggtgggaag catgcaggta gatgtggtgc tggaggaacc   1920
aagagttcta tatcctgatc tgaaggcagc caggagaaga ctgcctcttc tgcacagggc   1980
agagcttgag catagaacat caaagccctt ccccacactt cctccaacaa ggtcatacat   2040
acttcaacaa agacacacct cctaacggtg ccactccctg tggaccaacc atttaaacgc   2100
atgagtctat gagggtcaaa gctcttcaaa ccaccacact catgtacaca cacacacaca   2160
cacacacaca ctctcataca cacacacaca cacactcaca cacacacaca cacacacaca   2220
cacacacaca ccacacacac acacacacac agagttctat tttgcactgt ttcactgtca   2280
caaggttcta cttatctcag acacactgcc aggaattgtg tgggaagact ttcagtttct   2340
ttgggttcac atggacttag cagttcttgg tgatcctgaa agatttctgc agaaagaagc   2400
caaagtgttg agcccaaggc ctggccacac attagtcctg tctagatgaa caggggttta   2460
aaaataaggg ggcatcaagg tgaagccagc aggggctgac ttagagagga gacccaccca   2520
agccaactgc tcgaagtcaa aagcgatgaa tccccatatc cagctgtgcc cggtgctgtc   2580
ttgctacatc tttagtaaat gttcttttag ttgtatgcgt atgaatattt tgcttgcata   2640
tatttgtgta caccataggt gttcctaggg cctatggagg ccagaagagg gcatcagatc   2700
ctttggaact ggaattatag acacttgtta cccatagagt agattgtggg aaatgagcct   2760
ttagtcttcg agagcggcca gtgctcttaa cctttggtcg tttctccagg tctttgagac   2820
tttattttct tggacatcag gacaggatcc agggctttga gcttgtttct tcagccagct   2880
ttcttttcat gtatattaaa ttttatgtta ttttgctttc tttttcccca agacagaatc   2940
acactctata tagctcaggc tgggtttgaa ttcagtttcc ctgtctcagt ctaccgggta   3000
atatgattac agatgtgagt ctgactttgg tatcaaagtc cccagccctt ctggatatgt   3060
```

-continued

```
gttttaagga tatcagatat atccttgatt tgctttgaat tttcttttta gttacaacat   3120
aattagttcc gtgtcacctg aatatgtgta tgtcacctac atagtcttcc ttcttctctt   3180
cttccctctc ccaccttccc aggtacctgt ctgtcttcat atccttgtgc tgagagtctt   3240
gttgagggag atgatgaccg agacagagcc actggggaag ggagatgggc tagtgcaggt   3300
cttcagagag gagctcgtga atattgtagc ccctttagtc cctggcatgt cctcttgtat   3360
agccaccgcc atgctgtggc ctggcagaag tgaataagtt gtccagctgt tgacaggcct   3420
gccctccaga cccagtctga tcccaagaaa gggcatctgt gtctgtctct gaggccgtaa   3480
gtgctgcctg gttgtctcca gcttgacttg acactccctc cttaataaga gtaccacaga   3540
acagggtctg cagagtccct gggccaggtc cctgtgctgt cctggaatgc caggcgtgaa   3600
tttcctgtga agtaggactt tgctcgccaa gctcccacgg cttgcccttc agatagccag   3660
aattatctgg taccctgcat tgccgttcaa tacgcagagt atcactggaa gcgcgcgcgc   3720
gcacacacac acacacacac acacacacac acacacacac acacgcccac tccatcttta   3780
aaccccaccc cccagcaacg gcggtgtaaa cactctccat caggaagctg aaacgcagtt   3840
gccctctgct ggggagatga aggcagcttg ctgggggcga ggaccgtgct agcaaccttc   3900
cctggtgcac acgggctctg gtgcatgacg ggaacggaaa cgcggaacta aagtcagtcc   3960
tgcttttttt tttttttttt tttttttttt tttttttttt tttttttttt ggcgttggtg   4020
gtggactgag tgacaatcag tgaaatcact taggttgttt ttctcttctt cgttgggttt   4080
gatagacggt gggagagggt cagaggagaa ggggagggat ggggagagag ggaggaggga   4140
ggggcgggag gcggggggcg aggaaaacgt gctaacttct ccaatcctac aagacaaagg   4200
tttggagaaa gccgcactga gtgacccagc agaaggaatc caggaatgtc cgctggaatc   4260
tgactgttga ttccagcgcc atgcagagaa tctaggctgg taggaacatt ctttgtccta   4320
tccgacataa taactccaac caacacggaa aagaaaggct atacaagtga agaaatggca   4380
ttttcacttt catgactata caatcacttc caggtagtaa cacgtgtcta gcacagcggt   4440
tctcaacctg gggggtcacga tcccccactt ttctgcatat cagacatttt tacgttgtta   4500
ttcataacag tagcaaaatt gcagctatga agtaacaatg aaatgcattt atggtgcgtg   4560
tgtgtgtgtg tggggggggta tcaccttaac atttactgta agaaggttga gaatactgct   4620
ccagcagcta gtgtgttgga cttaggttct gggtatatta ttagcaatag ccaaccagaa   4680
tccccaccca ccacagcatt gaggccccat gcagggcttg ctgggagagg cactgataag   4740
acttctttat gtatttattt agagacgaat actcattagg taggccaagc tagcgtcaaa   4800
ctcatggcaa ttctcctcct ccagtttcct aagtactgga ctcaggagtg tgttgccatc   4860
atatacagta aggatttatt gactgaagaa aatctcaagt ggctttggtt aatccctact   4920
acgccagagg ctgaggcagg aggcgcgcaa ggtcaaggct tgcctgggct acatatagag   4980
tgagctcaat tttgacactt ggtgcggtgt tagtagtaat agtaaagatg aaggtgtggc   5040
tcaggtgggg ccggtgattg gacacacttg ggtctcctg gtccatctgc agctgtgcaa   5100
caggaagagc ggagaatgag aggaaagaga gaaaagacag aatgagagag agggaggaag   5160
agagaaaaag gaaaagagag aggaaaggaa aaaggaaaat gaggaaagcg agaaagaaga   5220
aatgagaaag aggaaaggga gaaagaaatg agagagagaa aagaaaagac agaatgcgag   5280
agagggagga agagagaaaa aggaaaagag agaggaaagg aaaaaggaaa atgaggaaag   5340
cgagaaagaa gaaatgagaa agaggaaagg gagaaagaaa tgagagagag aaaagaaaag   5400
acagaatgcg agagagggag gaagagagaa aaaggaaaag agagaggaag ggaaaaagga   5460
```

-continued

```
aaatgaggaa agcgagaaag aagaaatgag aaagaggaaa gggagaaaga aatgagagag   5520
agaaaagaaa agacagaatg cgagagaggg aggaagagag aaaaaggaaa agagagagga   5580
agggaaaaag gaaaatgagg aaagcgagaa agaagaaatg agaaagagga aagggagaaa   5640
gaaatgagag agagaaaaga aaagacagaa tgcgagagag ggaggaagag agaaaaagga   5700
aaagagagag gaagggaaaa tggaaaatga ggaaagcgag aaagaagaaa tgagaaagag   5760
gaaagggaga aagaaatgag cgagataaaa gacagaattt gagagaggga ggaagaaata   5820
ggaaaagaga ggaaaggatg gagaaaagag agaaagaaag agagatgaaa gagagaaagg   5880
agaaatgaaa tgagagagag agagagacac aaagagccag agagagaaga aaaaagggga   5940
aagagaaaga gaaagaggaa ggctcctctt ggacacatct tcctttatct ttccctgggg   6000
accgccaaag cctggtggca tactgtacat tctgtacact gttcattcaa aacaggctct   6060
gtcttaaaga tggtctgagc ggtcagaaaa gggtattgtt aacttgtttg caaaactgcc   6120
tcaggagagt gctgagtgcg tgaaagttgc tgcccgttaa ggagaagtct ctactacttg   6180
tgatctcacc atcgaaaatt tctttaattg tctcctggtg ttctgggttt tgcagttttg   6240
tttctaagga tacattcttg ggtgatgtca caaagtcccc aaagacacgg tggagctgtg   6300
ttagatgggg aaagacagtc tgctgaggat ttatctggaa ctgtcagaag gaaaagaagg   6360
taaatggggc acttgggaaa gtggcctcta gtttgacttc tggcttagca aaggttgtgg   6420
ggagataagg catacacagt agttagcagg aggcaacagg gtcctgggag gacgcgaggc   6480
agaaggagag gctgggctga cagcatgcaa tcattgcata gtctccaaag gagattgcaa   6540
catggctgag ttttcagagg tcctacagag cccgtggtag agattctgtg ggttctgaga   6600
caacttgact ttagccagat ggtatttgag taatctggga gagagaaaac agctacagca   6660
aacagggcca catttagtga cgaaactctc actttgactg ttgagtcatt tgcagtgggc   6720
cctgaggtca ggctggccct cagctcaaaa acaagcgagg aactgaagca attactcaga   6780
taatccacag ccacagccac tggaaagggc cacatcccca gagacagcac agcaggggtg   6840
ggggtggggc tatgagaaag ttagtgattg tagcagttat ctagaatgtg cggagcagag   6900
gaggttacac aaaaacctag aatgtcattc aatgtgggaa accgagaggc tcccaagccc   6960
taaaaggaac agtttgcttt cagccaaaat ggaaataaaa tttggggctt aaatctggca   7020
aatgattcag accttctgtg taggtgtctt taaatgcaca gcagattgat tttcatgttg   7080
gagtttattt gaactaaaag acagaaatgg tgaaaagcac acctgaagaa attgagatgc   7140
tatgaataaa atcatttact tacagctatc acttaattag tacctccttc caccttgctg   7200
atttattggg ctagtcaagg aagaaaagat cttccctcct ccttctctcc tcctccccct   7260
cctctcctcc tcccctcccc tccttgacct tcctctcctc cttttccctc ctccccctct   7320
tcttctcttc acccccctcct cccctcccct cctctgtact cctccccttt cctcccaatc   7380
tctttttct ccccccttctt ctctttctcc cccctcctct tccctcctct tcctccctcc   7440
ctccctcctc ctcctcatcc tcctcttcct cttcatcctc ttctccttcc tccctctcct   7500
cctcctcctt ttccagccct acctaccttc cctttcttct tcatttattc aaagtagctt   7560
tgaacagcac tactcggttt agttgtgtat aaaaggaaaa tgcaggtcca agcagcttgg   7620
ggaagattgc tttttgctct ctggaggcag atgatgacag ttcaagatca ttccttttgc   7680
tccatgtcac aggaaggggg acatgccgaa tctaccagtt tgcagccacc tacacaggat   7740
ccaccttcac ttctaaggaa atgtttggga agctacctac caaccacttc tggcatctca   7800
```

-continued

```
tgggctagag gactcttaaa tggcactctt atttgtttaa taaaggaggt tgtgacgtgt   7860
agttttaaat cccttccaca caacaattgc tactctctga ccaaaaaaga agggagacag   7920
gatacggcta ggtgtctagt agactttacc actttgaaaa gccttaatat aaatcaggta   7980
gatacatctt tttaacttat tcttgtaaag acaaaaacaa aactttattt ttatttgtgt   8040
gtatgcttgt gtgtgtgtgc ctgtgtgtat accacatgtc gctggtgccg gagaacacca   8100
gaagagggga cctgatctcc tggagctaaa gctatccatg gttctgagct gcctgatgtg   8160
ggtgctggga acagaactct ggtcttctgc aagagcaaca agcctcctct taactacgaa   8220
tctcctcccc atccccccaa atacatttaa ttattcattt tagcagcttt atttcgtaac   8280
tacttatcac agcataaaac aaggatttta tatatattac atgcaatcga ggataagagt   8340
tgaggggaga tgcgtgtgct ccttctgggt gtctgtgctt ttgaagaatg taagcagtgc   8400
acaagggacc gaggcgtgcc tgtctgccag gagctgtctt cttcccttgg actctgagct   8460
gagtgcagtg ctccgaagaa gtaaaagacg acctcatgaa gcaatgtctt caacccaaac   8520
atgctgtcca gacaaagtcc agcttcatta gtgctctgag gagagactta ctgagcctca   8580
ggaaagcccc cctcagcatg gcgaaagtcc actttgattg aagtgactcg aaagccatgg   8640
cagtgcggcg gcggccgcgt ggagcttgtg ctcgagtcgg aagcggcatc tttgtcaggc   8700
ggctgtgatt agcacgggga ggcaggactg gagtgaagga agagttgggg gcggggctta   8760
gcgctctggt ctcctaagct gtagtcagcg cctcaagatt tgtaacctgc cttctgcctt   8820
cccagccagg cagtcaagtg gctccaagct gaagactgca aagtgcccct aacctttgg    8880
ttatagcgag gctgaagaca ccgtgctctt tcatgaaagc cggatgtctg aaatccgatt   8940
tgataaatat ggataaaacg tataacgctc gatcaatcga atcgaaggag ctcacgattg   9000
gcaccacggc tttggggaca acagagtact gactcgttgg gaggacttgg atacttcccc   9060
tcctcttcca tctcttcccc tttcctcact tcctcctcct tccttctcca ttttctccct   9120
cttcactgtt tcttactatt tttacaaaag atttattta tttatttatt tatttattta    9180
tttatttatt tatttattta tttatttaat gtatgcgagt acactgtagc tgtcttcaga   9240
cacaccagaa gagggcgtca agttccatta gagatggttt cgagccacca tgtggttgct   9300
ggggcctctg gaaggaccgc cagtgctctt aacccctgag ccatttctcc agtacccttc   9360
tcaccgtttc tcttcaatct tcttcctctt ccttctccac tttccttgtc ttcttggttt   9420
cattatcttt ctccctttct tcctcttctc cccttcttcc tcctccactg tagttttcct   9480
tccctactct tttcctgcct ccctcctcct cccctctcat tccccctcct ctttcctcct   9540
tctccctcct cctccttcct tctccctctc ccctctcccc tctcccttct cccttctccc   9600
cctcctcttc ctctttctcc ttctccaccc ctcctgtcac agtatcaatg gcaagggtgt   9660
tctagaatgg aggagtgtcc cctaggcact aacgaaagcc agttaggatg ctctgagacg   9720
ggtacaattc agggagggcc gtggggatgg aagggttgtg ctgcgattca ttctggagca   9780
acccccaggc agaatcatga ggttggttcc ggattcgcag ggcacaattc agaagaggaa   9840
ggtttcagga aggacgagtt tgtctgagat aggagttaca tctgatgtct tggcagcaga   9900
gccactgtac aagcgtgctt tattaaccac gtgggattaa atcttctttt aaatttattt   9960
tcaactctta aggaaacgtg aactttcaca ttcaaattta gacttgcagc tcttatgggg  10020
aaaaaaaggg gatcttaaga atattaagca taggcggctg gagagatggc tcagcggtta  10080
agagcactct ctgctctccc agaggtcctg agttcaattc ctagcaacca cataatagtt  10140
aacaacagtc tttaatgaat tctaatgccc tcttctggtg tgtctgaaga cagttacagt  10200
```

-continued

```
gtactcatat aaataaaata aagaaattta aaaaaatgaa tattaggcat agattcctgg  10260
atcctaagaa agccatcaga gctggagcca tgtgtgggat cctgcttggt gctggagggg  10320
cagagttcat gcccccgggg tttttactta ttatcacatt ttcatcgttg ttttgaaaca  10380
gggtcttgtg tggtccaggc tggccttgaa ctcatctttc agcctctacc tcacaggttc  10440
tgggattact tggttcctaa aagtatctcc gtcaagctcc ctggtgttat ggctgtgcca  10500
accaggaggg tctatacact cgctcaggta gagggagaag atccgaatct ctgacaggga  10560
ctgctgcctc tcggggcaaa tggagtgaag gacagcggca gaaggattta ggaaagatgg  10620
acgggagagt ggaaatgctg cagaagccag aaaacaaagc aggaagcctg ctgtccagtg  10680
gggctcaaga gcggagggat gcgagggggc tgcgcaggaa catttagcgt ctgcgtctat  10740
gggggtaggg gcggggtgcc agcacctagt cacctgaagg ggaaatgctt gcccagggag  10800
caggtctcag tagctgacct agagaaagga gcggccccta cagaggagac acgggtcact  10860
gtttgttaaa gtgaaggaga aataaatatt ctttcaaaga atcttaggtg agcccagttc  10920
atctgcgctg tggaggcctg gggaacagtt aaaaagaccc tgacacacac ccaaggcaaa  10980
caagcaacac acggctcctt ccgtaagggt ccatgattct ctgaagaatc agccccggaa  11040
tcagccccgg aatcaggtag tccgtaaaca caatgagtgt tttactctgc agaagtccag  11100
cctgctggcg tctcccatta ccaaaataga gggatagtca cgtgagctca ccggctcgat  11160
ttaaggcacg tggttttcca gggtagatga gctttggctt ctggaaccat tatggggcac  11220
gaaggatgga gccaggattt tttttttttt tttttttttc tattagcaat tgatttgctt  11280
gggcttggct ggacttgccc agttcttagg cccagtcttc ttaactgccg atctgaagtc  11340
tgtcatggag tcagcctagc cttctcactt cccttcagct cgaataggaa gaggaggtgc  11400
acaccagatg gtctgagagc agggataaat ggtgtgcctt tgtctttcag tatttcgtta  11460
ttttaagtag gaagatgctt ttctgtatta cattgcttgt gaaaccggaa gttgattcgg  11520
ggcacaggac aatggatttg gtgttttgca aggactgttt cagaagagag aggagtggaa  11580
gggtggttag agtgaggagt ggggtgggac gggatggggg aagagaagga agggccagac  11640
aggctaggta gggctgagag gaggcggtgg gaacttcttg agttagcgca gcagtaaact  11700
tggatgtgcg tgtatctttg tgatatatga cccggagccg tgtagctggc tccgatagta  11760
ctgctaatgt cagtgtcggg gggggggggt cccatactgt tccacagggg ctgcacattc  11820
ccatcgagag caggagggct cctctctcca tacatcctcg ccagcattcc ttgttgtttc  11880
tgtgatgaca gggggtggga tgaaatctct ctgttggttt gagagaccgt gaagaagctc  11940
aaccccagga cattttgcag tcttggaagg cagtgcctcc atgtggagcc gtggagccca  12000
tctctgagtc caggtcactc ttgcagttcg cactcagctc ttcagatgca ggagagacgt  12060
tggtgggaaa gcaagattgt ttgcttgttg agatagacac attctccaca caaaggctca  12120
cgtggggcaa aggctgattg acgtacagcg ttcaggaacg cctgtggtag agctatgatt  12180
agctgtctcc atctatgaag cagacaaaga gttataaaaa aaatcaatgt tttcaaattg  12240
tcaaactttt aacccgacag caagcgctct gtccctgggc taatccctag ccctggtttc  12300
ttgagatggg gtcttttgtg cactagactg gcctagaact cacgatctta gtgttccagc  12360
ctcccagctg ctgggatgag ccgctataac cagtctgcct gccttcctaa attttaagtg  12420
atgggaagtg ggggagaata cagtttaaag tatgcagatc tgagagcagg aacctggcaa  12480
agccaagggg ccggagttac aggcggctaa catgggtgct gggaactgac ccaggtcctt  12540
```

-continued

```
gagaggagca gtgtgtactc ttgaccaaac aggtccgtct ctccagtccc cgtagtatta  12600

aaaataggta ctacgggcat ggtggtgcac acctttaatc ccagcactag ggaggcagag  12660

gcaggtggat ttctgagttt gaggccagcc tggtctacaa aatgagttcc aggacagcca  12720

cggctataca gagaaaccct gtcttgaaaa caaaacaaca acaaaatagg tactacaaag  12780

cgatgtaatt gtgctcaaac atgcaaaccg aggggactgt atgcataaga aagagaaaga  12840

cggccacact ggttctatct gggtgacagg aaatcagtat ttttattttt cacattcatt  12900

tttttgttgt tgttgttgac acagtgattt ttctatcaaa aacattattt cttttatagt  12960

tcccctgagg agctgttttt aaagccgtgc tttgaaaaac cattgaagga gcagaggcag  13020

ggagactcct gtgtggcagt cggtgaagca ggccctctgc aggcaggctg gccctggact  13080

tgggagtctc tttccctccc tcctgtgctc aaatagcaaa tgtcaggctt caatgtagct  13140

agaaggttct agaatgatta agtttccaag gctgaagagc ttccctgttt gcctttcact  13200

tccctggaga ggtcgttgtg tgttccggag tctgcaaggt gcctttggtg atgcgggtgg  13260

ttcatctcgg gagattccgc ctggaggacc caagttcaag ccctgcctga gctacagagt  13320

gactttcagg tcttctgcgc aattcagtga gacccagtct acaaataaaa agtaaaaaga  13380

aggctgtgga tggaactcgg tggtagagtt ctgggtttac tccctagagg aggggagaag  13440

gaggaggagg gaggaggaag aggaagaaag aagaagagaa gggaagagga gaaggaaggg  13500

agggaagggg ctgacaagaa gagagaagag ggagggaggg gagggaaagg aaggggaaag  13560

gaagggaggg aaggggctga caagaagaga gaagagggag ggaggggagg gaaaggaagg  13620

ggaaagaaga gaagggtaag aagaaactgt tccaatggtc tgggccacag agtgatggcc  13680

ttttgtggtg atcagctgta atccttgatt tgacacaacc tagaatctgg gaagcgagtt  13740

tctgtgaagg agcattcaca ctggctggcc tgtgggcgtg catgtgggag actgtcataa  13800

ttaggttcat taatacagga agtcccagcc cactacaaat ggcttcgttc catacccaag  13860

agatgctaac tgtagacggt tggagaaagc aagcaagctg tggatacccc acgctctttc  13920

acctcggctc ctggggggtg ggtgcactgt gtctcttggt attttaaagt cctgccttga  13980

cgtccctgct gtgacagact gtaactggaa ttgtgagctt tagtccttta gttttctacg  14040

ttggtttttc tcaggatatt ttatcgcagt aacagaaaca agaccaggac acttgatctc  14100

ctctgatcaa cactgaagag ttacaaaaca ggctgaggaa acaaactttc ttctccctct  14160

ccccccttctg tccctcccct tccttctcgc tccctccctt gccccctctc tccctgtctc  14220

tgtctctgtc tctgtctctg tctctgtctc tgtctctgcc tctcccctcc cctcccctcc  14280

ctctgtctct gtctctgtct ctgtctctgt ctctgtctct gtctctgtcc ctttctcctc  14340

tatctcctaa atggctggag gccatgctag ctcaatgttg aactttgaac acgtatttag  14400

gaaatctttg ttcttaacag ttctgaagtg ctgaagtggt ggtttagtct ctcggcctga  14460

caagctcact tcctctcact ctgtcttaat gaccaaatct gccatttccc taaaacagca  14520

caggctccag ctccaggttg ctccggagcg gag                               14553
```

<210> SEQ ID NO 7
<211> LENGTH: 34
<212> TYPE: DNA
<213> ORGANISM: Artificial Sequence
<220> FEATURE:
<223> OTHER INFORMATION: Synthetic

<400> SEQUENCE: 7

```
ataacttcgt ataatgtatg ctatacgaag ttgt                              34
```

-continued

```
<210> SEQ ID NO 8
<211> LENGTH: 34
<212> TYPE: DNA
<213> ORGANISM: Artificial Sequence
<220> FEATURE:
<223> OTHER INFORMATION: Synthetic

<400> SEQUENCE: 8

ataacttcgt ataatgtata ctatacgaag ttag                                34
```

ENHANCED EXPRESSION AND STABILITY REGIONS

CROSS-REFERENCE TO RELATED APPLICATIONS

This application claims benefit under 35 USC 119(e) of U.S. Provisional application No. 60/933,213, filed 4 Jun. 2007, which application is herein specifically incorporated by reference in its entirety.

BACKGROUND

1. Field of the Invention

The invention provides for expressing recombinant proteins in eukaryotic cells. In particular, the invention includes methods and compositions for improved expression of proteins in eukaryotic cells by employing expression-enhancing nucleotide sequences. The invention includes enhanced expression and stability region (EESYR) sequences that facilitate enhanced and stable expression of recombinant proteins in eukaryotic cells, and methods of using such sequences.

2. Description of Related Art

The development of expression systems is an important goal for providing a reliable and efficient source of a given protein for research and therapeutic use. Recombinant protein expression in mammalian cells is often preferred for manufacturing therapeutic proteins due to, for example, the ability of mammalian expression systems to appropriately post-translationally modify recombinant proteins.

Several vectors are available for expression in mammalian hosts, each containing various combinations of cis- and, in some cases, trans-regulatory elements to achieve high levels of recombinant protein with short incubation times. Despite the availability of numerous such vectors, the expression of a recombinant protein achieved in mammalian systems is often unacceptably low or otherwise unsatisfactory. Moreover, developing a cell line that reliably expresses sufficiently high levels of a desired protein often requires time consuming cloning and amplification steps. Accordingly, there is a need in the art for improved mammalian expression systems.

BRIEF SUMMARY

In one aspect, an isolated nucleotide sequence comprising an expression-enhancing sequence selected from a sequence of SEQ ID NO:1-6, or an expression-enhancing fragment thereof, is provided.

In one embodiment, the expression-enhancing sequence comprises an expression-enhancing sequence of SEQ ID NO:5 located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, an expression-enhancing sequence is provided that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5.

In another embodiment, the recombination recognition site is positioned as described above, providing that the expression-enhancing sequence comprises a sequence that is at least 90% identical, more preferably at least 95% identical, most preferably at least 99% identical, to the expression-enhancing sequence of SEQ ID NO:5 or an expression-enhancing fragment thereof.

In one embodiment, the expression-enhancing sequence further comprises at least one recombinase recognition site comprising a sequence independently selected from a loxp site, a lox 511 site, a lox 2272 site, and a frt site. In one embodiment, the recombinase recognition site is within the expression-enhancing sequence. In another embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites of opposite orientation are present within the expression-enhancing sequence. In another embodiment, three recombinase recognition sites are present within the expression-enhancing sequence.

In one aspect, an isolated nucleotide sequence is provided that comprises an expression-enhancing sequence that is at least 80% identical, preferably at least 90% identical, more preferably at least 95% identical, most preferably at least 99% identical to an expression-enhancing sequence of SEQ ID NO:1-6 or an expression-enhancing fragment thereof. In one embodiment, the expression-enhancing sequence displays the recited identity to a sequence of SEQ ID NO:5 as described above.

In one aspect, an isolated eukaryotic cell is provided that comprises an expression-enhancing sequence selected from SEQ ID NO:1-6 or an expression-enhancing fragment thereof. In one embodiment, the expression-enhancing sequence comprises an expression enhancing sequence of SEQ ID NO:5 as described above.

In one embodiment, the eukaryotic cell is a mouse, rat, hamster, or human cell. In a specific embodiment, the eukaryotic cell is a CHO cell.

In one embodiment, the eukaryotic cell further comprises at least one recombinase recognition sequence within the expression-enhancing sequence. In a specific embodiment, the at least one recombinase recognition sequence is independently selected from a loxp site, a lox 511 site, a lox 2272 site, and a frt site. In one embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites are of opposite orientation and are present within the expression-enhancing sequence. In another embodiment, three recombinase recognition sequences are present, and one of the three recombinase recognition sequences is in an orientation opposite to the two remaining recombinase recognition sequences.

In one embodiment, the recombinase recognition site in the expression-enhancing sequence of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, the recombinase recognition site in in a sequence that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5. In a specific embodiment, the recombinase recognition site is located within nucleotides 6400-6500 of SEQ ID NO:5. In another specific embodiment, the recombinase recognition site is inserted before, after, or within the "act" triplet of nucleotides 6471 to 6473 of SEQ ID NO:5 in an expression-enhancing sequence of SEQ ID NO:5.

In another specific embodiment, the recombination recognition site is positioned as described above, with the caveat that the expression-enhancing sequence comprises a sequence that is at least 90% identical, more preferably at least 95% identical, most preferably at least 99% identical, to nucleotides 5218 through 6048 of SEQ ID NO:5 or an expression-enhancing fragment thereof.

In a specific embodiment, the cell is a CHO cell and the recombinase recognition site is inserted in the CHO cell genome at or within the "act" triplet of nucleotides 6,471 to 6,473 of SEQ ID NO:5.

In one embodiment, a first GOI is inserted within the expression-enhancing sequence of SEQ ID NO:5 as described above, and the first GOI is optionally operably linked to a promoter, wherein the promoter-linked GOI (or the GOI) is flanked 5' by a first recombinase recognition site and 3' by a second recombinase recognition site. In another embodiment, a second GOI is inserted 3' of the second recombinase recognition site, and the second GOI is flanked 3' by a third recombinase recognition site.

In a specific embodiment, the GOI is operably linked to a promoter capable of driving expression of the GOI, wherein the promoter comprises a eukaryotic promoter that is regulatable by an activator or inhibitor. In another specific embodiment, the eukaryotic promoter is operably linked to a prokaryotic operator, and the eukaryotic cell optionally further comprises a prokaryotic repressor protein.

In another embodiment, one or more selectable markers are included between the first and the second and/or the second and the third recombinase recognition sites. In a specific embodiment, the first and/or the second genes of interest and/or the one or more selectable markers are operably linked to a promoter, wherein the promoter may be the same or different. In a specific embodiment, the promoter comprises a eukaryotic promoter (such as, for example, a CMV promoter), optionally controlled by a prokaryotic operator (such as, for example, a tet operator). In a specific embodiment, the cell further comprises a gene encoding a prokaryotic repressor (such as, for example, a tet repressor).

In another embodiment, the cell further comprises a gene capable of expressing a recombinase. In a specific embodiment, the recombinase is a Cre recombinase.

In one aspect, an isolated eukaryotic cell is provided that comprises an expression-enhancing sequence that is at least 80%, more preferably at least 90%, more preferably at least 95%, most preferably at least 99% identical to an expression-enhancing sequence of SEQ ID NO:1-6 or an expression-enhancing fragment thereof. In a specific embodiment, expression-enhancing sequence is a sequence within SEQ ID NO:5 as described above.

In one aspect, a eukaryotic host cell is provided, comprising an expression-enhancing sequence selected from SEQ ID NO:1-6 or an expression-enhancing fragment thereof, comprising a first recombinase recognition site followed by a first eukaryotic promoter, a first marker gene, a second eukaryotic promoter, a second marker gene, a second recombinase recognition site, a third eukaryotic promoter, a third marker gene, and a third recombinase recognition site. In one embodiment, the expression-enhancing sequence is within SEQ ID NO:5 as described above.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a puromycin resistance gene. In another embodiment, the second and third marker genes encode two different fluorescent proteins. In one embodiment, the two different fluorescent proteins are selected from Discosoma coral (DsRed), green fluorescent protein (GFP), enhanced green fluorescent protein (eGFP), cyano fluorescent protein (CFP), enhanced cyano fluorescent protein (eCFP), and yellow fluorescent protein (YFP). In a specific embodiment, the two different fluorescent proteins are eCFP and DsRed.

In one embodiment, the first, second, and third promoters are the same. In another embodiment, the first, second, and third promoters are different. In another embodiment, the first promoter is different from the second and third promoters, and the second and third promoters are the same. In a specific embodiment, the first promoter is an SV40 late promoter, and the second an third promoters are each a human CMV promoter.

In one aspect, a eukaryotic host cell is provided, comprising an expression-enhancing sequence selected from SEQ ID NO:1-6, or an expression-enhancing fragment thereof, at least one recombinase recognition site within the expression-enhancing sequence, and at least one gene of interest (GOI) within the expression-enhancing sequence. In one embodiment, the expression-enhancing sequence is a sequence within SEQ ID NO:5, as described above.

In one embodiment, the cell comprises a first recombinase recognition site followed by a first promoter operably linked to a first GOI. In another embodiment, the first GOI is followed by a second recombinase recognition site. In another embodiment, the second recombinase recognition site is followed by a second promoter operably linked to a second GOI. In another embodiment, the second GOI is followed by a third recombinase recognition site. In another embodiment, at least one marker is operably linked to a third promoter and is located between the second recombinase recognition site and the second promoter. In one embodiment, the first recombinase recognition site is oriented in an opposite orientation to the second and third recombinase recognition sites. In one embodiment the first and second promoters are eukaryotic promoters operably linked to a prokaryotic operator. In one embodiment, the first and second promoters are CMV promoters operably linked to tet operator sequences. In another embodiment, the cell further comprises a gene capable of expressing a prokaryotic repressor. In one embodiment, the prokaryotic repressor is a tet repressor. In one embodiment, the cell comprises a gene capable of expressing a Cre recombinase.

In one embodiment, a first and a second marker gene are located between the second recombinase recognition site and the second promoter, and an IRES is between the first and second marker genes. In another embodiment, the first codon (ATG) of the first marker gene is immediately 5' to the second recombinase recognition site, and the second codon of the first marker gene is immediately 3' to the second recombinase recognition site. In another embodiment, the first marker gene contains an intron and the second recombinase recognition site is located within the intron such that the amino-terminal half of the first marker gene and the 5' half of the intron are located 5' of the second recombinase recognition site and the 3' half of the intron and carboxy-terminal half of the first marker gene are immediately 3' to the second recombinase recognition site.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a hygromycin resistance gene. In another embodiment, the second marker gene encodes a fluorescent protein. In one embodiment, the fluorescent protein is selected from DsRed, GFP, eGFP, CFP, eCFP, and YFP.

In one embodiment, the first, second, and third promoters are the same. In another embodiment, the first, second, and third promoters are different. In another embodiment, the third promoter is different from the first and second promoters, and the first and second promoters are the same. In a specific embodiment, the third promoter is an SV40 late promoter, and the first and second promoters are each a human CMV promoter.

In one embodiment, the first and second promoters are operably linked to a prokaryotic operator. In a specific embodiment, the operator is a tet operator.

In one embodiment, the host cell line has an exogenously added gene encoding a recombinase integrated into its genome, operably linked to a promoter. In a specific embodiment, the recombinase is Cre recombinase. In another embodiment, the host cell has a gene encoding a regulatory protein integrated into its genome, operably linked to a promoter. In a specific embodiment, the regulatory protein is a tet repressor protein.

In one embodiment, the first GOI and the second GOI encode a light chain, or fragment thereof, of an antibody or a heavy chain, or fragment thereof, of an antibody. In a specific embodiment, the first GOI encodes a light chain of an antibody and the second GOI encodes a heavy chain of an antibody.

In one aspect, a method is provided for making a protein of interest, comprising: (a) providing a host cell that comprises an expression-enhancing sequence selected from a sequence of SEQ ID NO:1-6; (b) introducing into the host cell, within the expression-enhancing sequence, a gene of interest (GOI) operably linked to a promoter; (c) maintaining the host cell of (a) under conditions that allow the GOI to express a protein of interest; and, (c) recovering the protein of interest.

In one embodiment, the cell is a CHO cell and the nucleotide sequence is an expression-enhancing sequence of SEQ ID NO:5 as described above.

In one embodiment, the GOI is introduced into the cell employing a targeting vector for homologous recombination, wherein the targeting vector comprises a 5' homology arm homologous to a sequence present in at least one of SEQ ID NO:1-6, a GOI, and a 3' homology arm homologous to a sequence present in at least one of SEQ ID NO:1-6. In another embodiment, the construct further comprises two, three, four, or five or more genes of interest. In another embodiment, one or more of the genes of interest are operably linked to a promoter.

In another embodiment, the GOI is introduced employing an integrase technology, for example, integrase technology employing att sites such as Invitrogen's Gateway™ and Multisite Gateway™ cloning systems which employ bacteriophage lambda att site recombination.

In another embodiment, the expression-enhancing sequence comprises one or more recombinase recognition sites as described above, and the GOI is introduced into the expression-enhancing sequence through the action of a recombinase that recognizes the recombinase recognition site.

In one embodiment, the expression-enhancing sequence comprises two recombinase recognition sites.

In one embodiment, the expression-enhancing sequence comprises a first, a second, and a third recombinase recognition site. In one embodiment, the first, second, and third recombinase recognition sites are different. In another embodiment, the first, second, and third recombinase recognition sites are not in the same orientation. In a specific embodiment, the first site is 5' to the second site, and the second site is 5' to the third site. In another specific embodiment, the second and third sites are in opposite orientation with respect to the first site.

In another embodiment, a first and a second GOI are introduced into the expression-enhancing sequence. In one embodiment, the first GOI is introduced between the first and the second recombinase recognition sites, and the second GOI is introduced between the second and the third recombinase recognition sites. In a specific embodiment, the recombinase recognition sites are independently selected from a loxp site, a lox 511 site, a lox 2272 site, and a frt site.

In another embodiment, the first GOI flanked by recombinase recognition sites on a first vector and the second GOI flanked by recombinase recognition sites on a second vector are introduced into a cell comprising an expression-enhancing sequence that comprises three recombinase recognition sites in a single step.

In one embodiment, the GOI is operably linked to a eukaryotic promoter. In another embodiment, the eukaryotic promoter is operably linked to a prokaryotic operator. In a specific embodiment, the eukaryotic promoter is a CMV promoter and the prokaryotic operator is a tet operator.

In another embodiment, the cell comprises a gene capable of expressing a prokaryotic repressor. In a specific embodiment, the prokaryotic repressor is a tet repressor.

In another embodiment, the cell comprises a gene capable of expressing a recombinase. In a specific embodiment, the recombinase is a Cre recombinase.

In one aspect, a eukaryotic cell is provided, wherein the eukaryotic cell comprises at least one expression-enhancing sequence of SEQ ID NO:1-6 and at least one exogenously added gene within the expression-enhancing sequence. In one embodiment, the exogenously added gene is operably linked to an exogenously added promoter.

In one embodiment, the expression-enhancing sequence is a sequence of SEQ ID NO:5, and the at least one exogenously added gene integrated or inserted within the expression-enhancing sequence is a human gene. In a specific embodiment, the eukaryotic cell is a CHO cell, the exogenously added gene is a human gene, and the human gene is operably linked to an exogenously added eukaryotic promoter.

In one aspect, a targeting vector for homologous recombination is provided, wherein the targeting vector comprises a 5' homology arm, a GOI, and a 3' homology arm, wherein each homology arm is homologous to a sequence within one of SEQ ID NO:1-6. In one embodiment, the 5' and 3' homology arms are homologous to sequences within SEQ ID NO:5. In one embodiment, the targeting vector comprises two, three, four, or five or more genes of interest. In one embodiment, the GOI is operably linked to a promoter. In another embodiment, each of the two, three, four, or five or more genes of interest are each operably linked to a promoter.

In one aspect, an expression vector is provided, comprising an expression-enhancing nucleotide sequence selected from SEQ ID NO: 1-6 or an expression-enhancing fragment thereof. In one embodiment, the expression-enhancing sequence is within SEQ ID NO:5 as described above.

In one embodiment, the vector further comprises a promoter. In a specific embodiment, the promoter is a human CMV promoter.

In one embodiment, the vector further comprises a cloning site for an expressible gene of interest (GOI). In one embodiment, the nucleotide sequence selected from SEQ ID NO: 1-6 or expression-enhancing fragment thereof is located 3' with respect to the cloning site for the expressible GOI. In another embodiment, the nucleotide sequence selected from SEQ ID NO: 1-6 or expression-enhancing fragment thereof is located 5' with respect to the cloning site for the expressible GOI.

In a specific embodiment, the vector comprises a nucleotide sequence selected from SEQ ID NO:1-6 or an expression-enhancing fragment, a human CMV promoter, a GOI, and a termination sequence, wherein the nucleotide sequence selected from SEQ ID NO: 1-6, or the expression-enhancing fragment thereof, is located 5' with respect to the CMV promoter. In a specific embodiment, the vector further comprises an intron selected from a CMV-MIE intron and a rabbit β-globin intron.

In one aspect, an expression vector is provided, comprising an expression-enhancing nucleotide sequence that is at least 80% identical, preferably at least 90% identical, more preferably at least 95% identical, most preferably at least 99% identical to a sequence selected from SEQ ID NO:1-6 or an expression-enhancing fragment thereof.

In one aspect, a method is provided for making a protein of interest, comprising: (a) introducing into a host cell an expression vector comprising an expression-enhancing sequence selected from a sequence within SEQ ID NO:1-6 and a GOI that encodes for a protein of interest, wherein the GOI is operably linked to a promoter and operably linked to the expression-enhancing sequence; (b) culturing the host cell of (a) under conditions that allow expression of the GOI; and (c) recovering the protein of interest.

In one embodiment, the enhanced expression and stability region sequence is an expression-enhancing sequence of SEQ ID NO:1-6. In one embodiment, the expression-enhancing sequence is within SEQ ID NO:5 as described above.

In one embodiment, the recombinant protein is selected from the group consisting of a subunit of an immunoglobulin or fragment thereof and a receptor or ligand-binding fragment thereof. In a specific embodiment, the recombinant protein is selected from the group consisting of an antibody light chain or antigen-specific fragment thereof, and an antibody heavy chain or antigen-specific fragment thereof.

In any of the aspects and embodiments described above, the expression-enhancing sequence can be placed in the indicated orientation as indicated in SEQ ID NO:1-6, or in the reverse of the orientation indicated in SEQ ID NO:1-6.

Any of the aspects and embodiments of the invention can be used in conjunction with any other aspect or embodiment of the invention, unless otherwise specified or apparent from the context.

Other objects and advantages will become apparent from a review of the ensuing detailed description.

BRIEF DESCRIPTION OF THE FIGURES

FIGS. 3A and 3B show an alignment of Chinese hamster ovary (CHO), mouse, human, and rat EESYR sequences for a fragment of SEQ ID NO:5.

FIG. 5 illustrates that an EESYR, operably linked to a gene of interest (GOI), exhibits enhanced expression over a GOI that is not operably linked to an EESYR. For each plot, major ticks on the y-axis represent 3, 300, 600, 900, and 1200; major ticks on the x-axis represent $10^0$, $10^1$, $10^2$, $10^3$, and $10^4$.

FIG. 6 shows EESYRs compared in their relative ability to enhance expression of an operably linked GOI. For each plot, major ticks on major ticks represent Counts of 0, 500, 1,000, 1,500, and 2,000; x-axis major ticks represent FITC of $10^0$, $10^1$, $10^2$, $10^3$, and $10^4$.

FIG. 10 illustrates testing of cis-acting elements employing EESYR sequences. Major ticks of the y- and x-axes represent $10^0$, $10^1$, $10^2$, $10^3$, and $10^4$.

FIG. 12 illustrates optimizing protein expression using an EESYR system.

DETAILED DESCRIPTION

Figure 1:
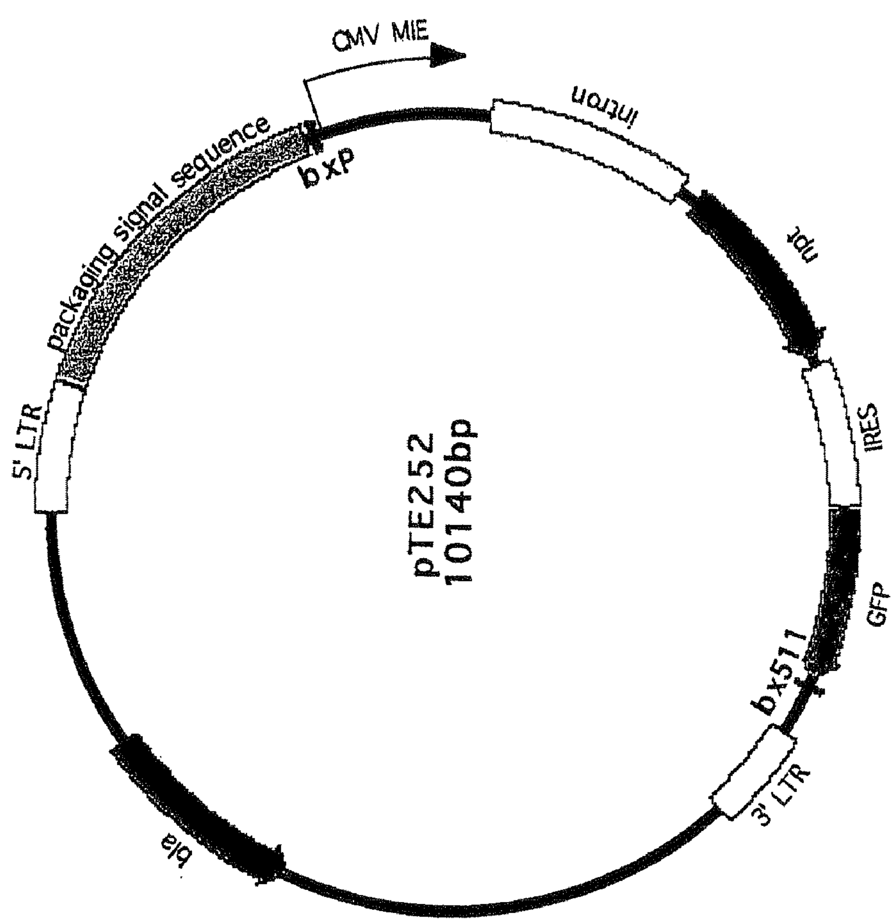
FIG. 1. Schematic diagram of a retroviral construct, pTE252, used for the introduction of nucleic acid construct into a cell genome. LTR: long terminal repeat; LoxP: Cre recombinase recognition sequence: ATAACTTCGTATAATGTATGCTATACGAAGTTGT (SEQ ID NO:7); Lox511: a mutation of LoxP sequences: ATAACTTCGTATAATGTATACTATACGAAGTTAG (SEQ ID NO:8); the Lox511 sequence is recognized by Cre recombinase but the Lox511 site does not recombine with a LoxP site. GFP: Green fluorescent protein; CMV MIE: human cytomegalovirus major immediate early promoter; npt: neomycin phosphotransferase; bla: beta lactamase; IRES: internal ribosomal entry site.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, or otherwise specified, all technical and scientific terms used herein have the same meaning as commonly understood by one of ordinary skill in the art to which this invention belongs.

Although any methods and materials similar or equivalent to those described herein can be used in the practice or testing of the present invention, particular methods and materials are now described. All publications mentioned herein are incorporated herein by reference in their entirety.

Definitions

DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An EESYR is operably linked to a GOI where it is functionally related to the gene of interest, for example, where its presence results in enhanced expression of the GOI.

The term "enhanced" when used to describe enhanced expression includes an enhancement of at least about 1.5-fold to at least about 2-fold enhancement in expression over what is typically observed by random integration into a genome, for example, as compared to a pool of random integrants of a single copy of the same expression construct. Fold-expression enhancement observed employing the sequences of the invention is in comparison to an expression level of the same gene, measured under substantially the same conditions, in the absence of a sequence of the invention. As used herein, the phrase "expression-enhancing" is used interchangeably with "enhanced expression and stability" when referring to a region or sequence. An "enhanced expression and stability region," also referred to herein as an "EESYR," is a region or sequence that exhibits more efficient recombination, insert stability, and higher level expression than is typically observed by random integration into a genome.

Enhanced recombination efficiency includes an enhancement of the ability of a locus to recombine (for example, employing recombinase-recognition sites). Enhancement refers to an efficiency over random recombination, which is typically 0.1%. A preferred enhanced recombination efficiency is about 10-fold over random, or about 1%. Unless specified, the claimed invention is not limited to a specific recombination efficiency.

Where the phrase "exogenously added gene" or "exogenously added GOI" is employed with reference to a EESYR, the phrase refers to any gene not present within the EESYR as the EESYR is found in nature. For example, an "exogenously added gene" within a CHO EESYR (e.g., an EESYR comprising a sequence of SEQ ID NO:5), can be a hamster gene not found within the CHO EESYR in nature (i.e., a hamster gene from another locus in the hamster genome), a gene from any other species (e.g., a human gene), a chimeric gene (e.g., human/mouse), or any other gene not found in nature to exist within the CHO EESYR.

General Description

The invention is based at least in part on the discovery that there are sequences in a genome that exhibit more efficient recombination, insert stability, and higher level expression than other regions or sequences in the genome. The invention is also based at least in part on the finding that when such expression-enhancing sequences are identified, a suitable gene or construct can be exogenously added in or near the sequences and that the exogenously added gene can be advantageously expressed. Such sequences, termed enhanced expression and stability regions ("EESYRs"), can be engineered to include recombinase recognition sites for placement of genes of interest to create cell lines that are capable of expressing proteins of interest. EESYRs can also be included as in expression constructs such as, for example, expression vectors. Expression vectors comprising EESYRs can be used to express proteins transiently, or can be integrated into a genome by random or targeted recombination such as, for example, homologous recombination or recombination mediated by recombinases that recognize specific recombination sites (e.g., Cre-lox-mediated recombination). Expression vectors comprising EESYRs can also be used to assess efficacy of other DNA sequences, for example, cis-acting regulatory sequences.

The CHO EESYR described in detail herein was identified by random integration of DNA comprising lox sites into a CHO cell genome, followed by selection to identify sequences where expression was enhanced. Random integration and introduction of the lox site was achieved using a retroviral construct. Selection and screening were achieved using drug resistance markers and detectable labels (e.g., fluorescent proteins with FACS screening), employing recombination methods that used site-specific recombination (e.g., lox sites and Cre recombinase). Selection continued until at least a 1.5- to 2-fold enhanced expression over expression observed when randomly integrating an expression construct into the CHO cell genome. Following identification of the EESYR, recombinase recognition sites (in the example provided, lox sites) were maintained in the EESYR for introducing expression cassettes that comprise an expressible GOI, along with any other desirable elements such as, for example, promoters, enhancers, markers, operators, etc.

Figure 2:
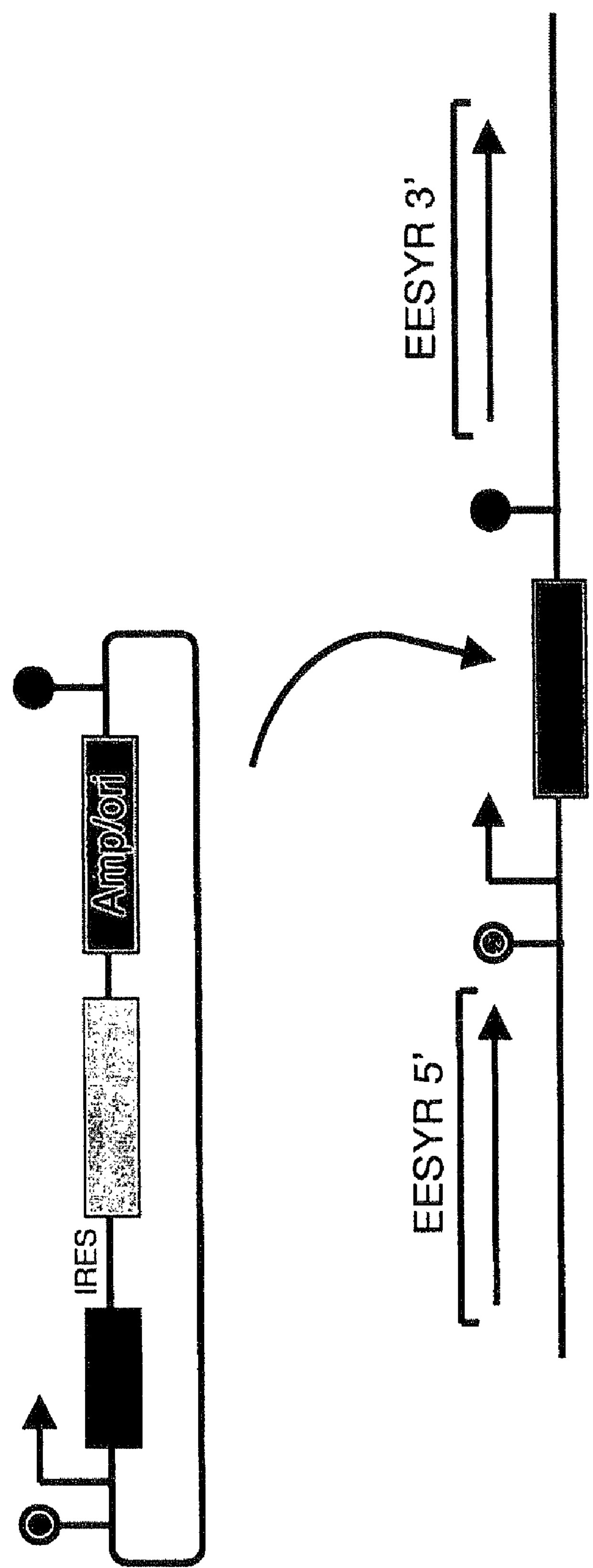
FIG. 2 illustrates a plasmid construct used to identify an EESYR.

An illustration of a plasmid construct used in identifying an EESYR disclosed in this application is shown in FIG. 2. The plasmid rescue construct comprises an expression cassette driven by an promoter, wherein the cassette is flanked on the 5' and 3' ends with recombinase recognition sites (represented by ball-and-stick in FIG. 2). Insertion within an EESYR locus is shown, wherein the insertion results in the plasmid rescue construct replacing an expression cassette that comprises a promoter and a marker, wherein the expression cassette within the EESYR locus is flanked on its 5' and 3' ends by recombinase recognition sites (see FIG. 2).

Compositions and methods are provided for stably integrating a nucleic acid sequence into a eukaryotic cell, wherein the nucleic acid sequence is capable of enhanced expression by virtue of being integrated in or near an EESYR. Cells are provided that contain a recombinase recognition sequence within or near an EESYR, convenient for inserting a GOI, in order to achieve expression of a protein of interest from the GOI. Compositions and methods are also provided for using EESYRs in connection with expression constructs, for example, expression vectors, and for adding an exogenous EESYR into a eukaryotic cell of interest.

Physical and Functional Characterization of an EESYR

The nucleic acid sequences referred to as EESYRs were empirically identified by sequences upstream and downstream of the integration site of a nucleic acid construct (comprising an expression cassette) of a cell line expressing a reporter protein at a high level. The EESYR nucleic acid sequences of the invention provide sequences with a new functionality associated with enhanced expression of a nucleic acid (for example, an exogenous nucleic acid comprising a GOI) that appear to function differently from that previously described for cis-acting elements such as promoters, enhancers, locus control regions, scaffold attachment regions or matrix attachment regions. EESYRs do not appear to have any open reading frames (ORFs), making it unlikely that EESYRs encode novel trans-activator proteins. Transfection experiments demonstrated that EESYR sequences display some characteristics of cis-acting elements. EESYR activity is not detected in transient transfection assays; EESYR sequences also appear to be distinct from promoter and enhancer elements, which are detected with these methods.

Although EESYR sequences described in detail herein were isolated from the genome of two cell lines, EESYR sequences from these two cell lines are the same. EESYR activity was identified in a 6.472 kb fragment of CHO genomic DNA 5' with respect to a unique integration site of a retroviral vector comprising a DsRed reporter encoding sequence and in a 7.045 kb fragment of CHO genomic DNA 3' with respect to the integration site. Expression vectors comprising the isolated 6.472 kb region and the isolated 7.045 kb region and shorter fragments thereof were able to confer upon CHO cells transfected with them high levels of expression of recombinant proteins.

The invention encompasses expression vectors comprising reverse orientated EESYR fragments. Reverse orientated EESYR fragments were also capable of conferring upon CHO cells transfected with them high levels of expression of recombinant proteins.

Other combinations of the fragments described herein can also be developed. Examples of other combinations of the fragments described herein that can also be developed include sequences that include multiple copies of the EESYR disclosed herein, or sequences derived by combining the disclosed EESYR with other nucleotide sequences to achieve optimal combinations of regulatory elements. Such combinations can be contiguously linked or arranged to provide optimal spacing of the EESYR fragments (e.g., by the introduction of spacer nucleotides between the fragments). Regulatory elements can also be arranged to provide optimal spacing of an EESYR with respect to the regulatory elements.

The EESYR sequences disclosed herein were isolated from CHO cells. Homologous expression-enhancing elements are expected to exist in cells from other mammalian species (such as, for examples, humans; see FIG. 3) as well as in cell lines derived from other tissue types, and can be isolated by techniques that are well-known in the art, for example, by cross-species hybridization or PCR-based techniques. In addition, changes can be made in the nucleotide sequence set forth in SEQ ID NOs:1-6 by site-directed or random mutagenesis techniques that are well known in the art. The resulting EESYR variants can then be tested for EESYR activity as described herein. DNAs that are at least about 80% identical, preferably at least about 90% identical, more preferably at least about 95% identical, most preferably least about 99% identical in nucleotide sequence to SEQ ID NOs:1-6 or fragments thereof having EESYR activity are isolatable by routine experimentation, and are expected to exhibit EESYR activity. For fragments of EESYR, percent identity refers to that portion of the reference native sequence that is found in the EESYR fragment. Accordingly, homologs of EESYR and variants of EESYR are also encompassed by embodiments of the invention. FIGS. 3A and B show an alignment of mouse, human, and rat sequences with varying homology to a fragment of SEQ ID NO:5.

Cell populations expressing enhanced levels of a protein of interest can be developed using the methods provided herein. The absolute level of expression will vary with the specific protein, depending on how efficiently the protein is processed by the cell. Cell pools developed with EESYR are stable over time, and can be treated as stable cell lines for most purposes. Cloning steps can be delayed until later in the process of development than is customary for recombinant proteins.

EESYRs and Expression-Enhancing Fragments Thereof

Figure 4:
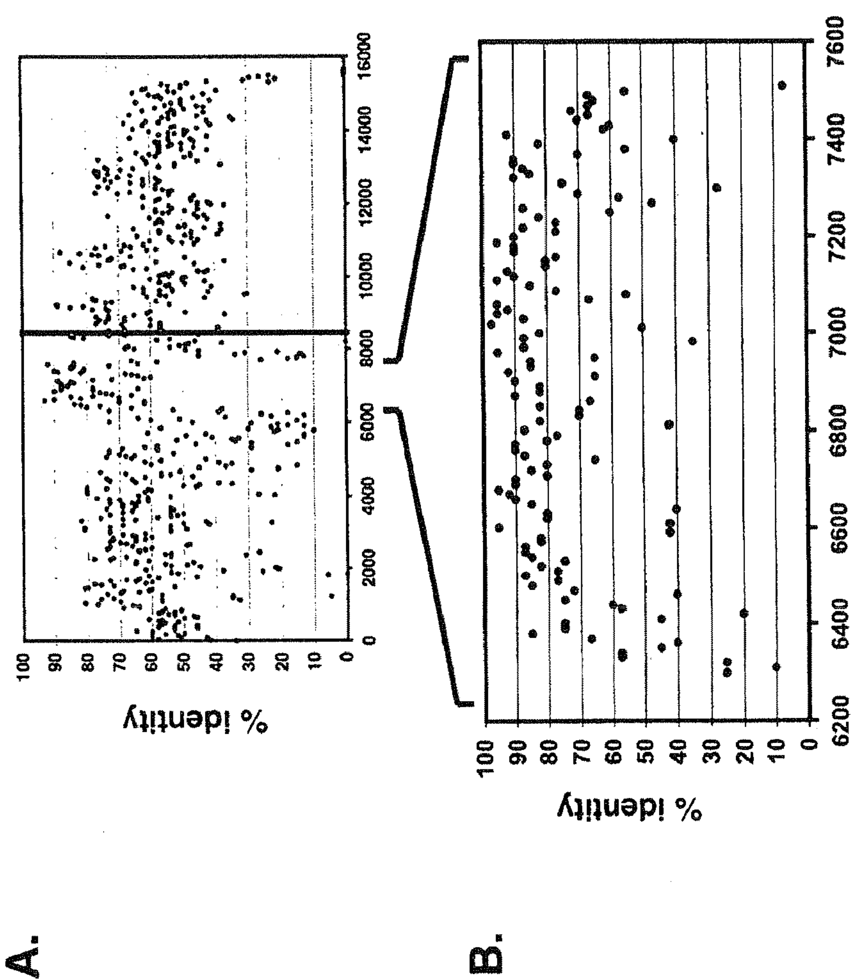
FIG. 4 shows an alignment of SEQ ID NO:5 with mouse, human, and rat sequences.

The EESYR genomic locus is conserved among human, mouse and rat genomes. FIG. 4 shows percent identity among EESYR sequences. EESYR sequences, homologous to the 13.515 kb of cloned CHO EESYR DNA of SEQ ID NO:5, were identified among the published human, rat and mouse genomes using BLAST. Sequences were aligned to determine the percent homology using MacVector (9.0). Twenty-five bp increments of the alignment are graphed as the percent identity among CHO, human, mouse and rat EESYR sequences for each consecutive 25 bp segment. As shown in FIG. 4, the vertical line marks the location of site-specific recombination events to express recombinant protein genes of interest. Percent identity of EESYR sequences adjacent to a site-specific recombination location in an EESYR is shown in panel B of FIG. 4. Ten base pair increments of the aligned sequences corresponding to nt 5022-6110 of a CHO cell EESYR sequence (nucleotides 5022 through 6110 of SEQ ID NO:5) are graphed as the percent identity among CHO, human, mouse and rat EESYR sequences for each consecutive 10 bp segment. Sequences were aligned using MacVector™ 9.0. As shown in panel B, a significant identity of sequence is present in this fragment of the EESYR cloned from CHO cells. It should be noted that the comparison of FIG. 4 indicates a length of about 1400 bases, whereas the sequence of SEQ ID NO:5 contains 13,515 bases. The FIG. 4 bases appear to extend over a longer stretch due to the existence of gaps. Nucleotide spans recited are those corresponding to numbering in SEQ ID NO:5 unless otherwise indicated. The span of nucleotides from about 6200 to about 7600 as shown in FIG. 4B corresponds to nucleotides of SEQ ID NO:5 numbered about 5,200 to about 6,000.

Accordingly, the invention also includes an expression-enhancing fragment of a nucleotide sequence of SEQ ID NO:5, wherein the expression-enhancing fragment includes the nucleotide sequence indicated by positions about residues 5022 through about 6110 of SEQ ID NO:5, or about 5218 through about 6048 of SEQ ID NO:5; or about 6200 through about 7600, about 6500 to about 7400, or about 6400 to about 6500 shown in panel B of FIG. 4. The invention also encompasses an expression-enhancing fragment of a nucleotide sequence that is at least 80% identical, preferably at least 90% identical, more preferably at least 95% identical, most preferably at least 99% identical to the nucleotide sequence indicated by positions about 6200 through about 7600, or about 6500 through about 7400, or about 6400 through about 6500 shown in panel B of FIG. 4. The invention includes vectors comprising such a fragment, including for transient or stable transfection. The invention also includes a eukaryotic cell comprising such a fragment wherein the fragment is exogenous and is integrated into the cell genome, and cells comprising such a fragment having at least one recombinase recognition site that is within, immediately 5', or immediately 3' to the fragment.

In one embodiment, the expression-enhancing fragment of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485.

In one embodiment, the EESYR is employed to enhance the expression of a GOI, as illustrated in FIG. 5. FIG. 5 shows a GOI operably linked with a promoter (with an upstream marker having its own promoter) integrated in a non-EESYR position in a CHO cell genome, and a FACS readout showing the distribution of expression in a stably transfected population of cells. In comparison, a GOI operably linked to a promoter integrated at an EESYR position in a CHO cell genome is shown, and a FACS readout showing the distribution of expression in a stably transfected population of cells is also shown. In this embodiment, the GOI expressed within the EESYR locus shows an enhanced expression of about two-fold in comparison to the GOI expressed at a non-EESYR locus.

In various embodiments, expression of a GOI can be enhanced by placing the GOI within an EESYR, 5' to an EESYR, or 3' to an EESYR. The precise distance between the GOI and the EESYR, where the GOI is either 5' or 3' to the EESYR, should be such that the EESYR is operably linked to the GOI. An EESYR is operably linked to the GOI where expression of the GOI—at the selected distance from the EESYR (in the 5' or 3' direction)—retains the ability to enhance expression of the GOI over, for example, expression typically observed due to a random integration event. In various embodiments, enhancement is at least about 1.5-fold to about 2-fold or more. Preferably, enhancement in expression as compared to a random integration, or random expression, is about 2-fold or more.

FIG. 6 shows an embodiment wherein SEQ ID NO:1 ("EESYR 5") and SEQ ID NO:2 ("EESYR 3'") are compared in their relative ability to enhance expression of an operably linked GOI, wherein the GOI is operably linked to a promoter as well (a marker and a promoter operably linked to the marker are shown 5' to the GOI promoter). Orientation of the EESYR is shown by the direction of the arrow beneath the term "EESYR." The constructs are randomly integrated into a CHO cell genome. Expression is relative to the randomly integrated construct that does not comprise any EESYR. FACS readouts showing relative expression are shown on the right. In FIG. 6, the first EESYR construct employs SEQ ID NO:1; the second EESYR construct employs SEQ ID NO:3; the third EESYR construct is SEQ ID NO:2; the fourth EESYR construct is SEQ ID NO:4. As shown in the figure, SEQ ID NO:3 displays a 2.4-fold enhancement in expression, and SEQ ID NO:1 displays a 2-fold enhancement of expression.

Figure 7:
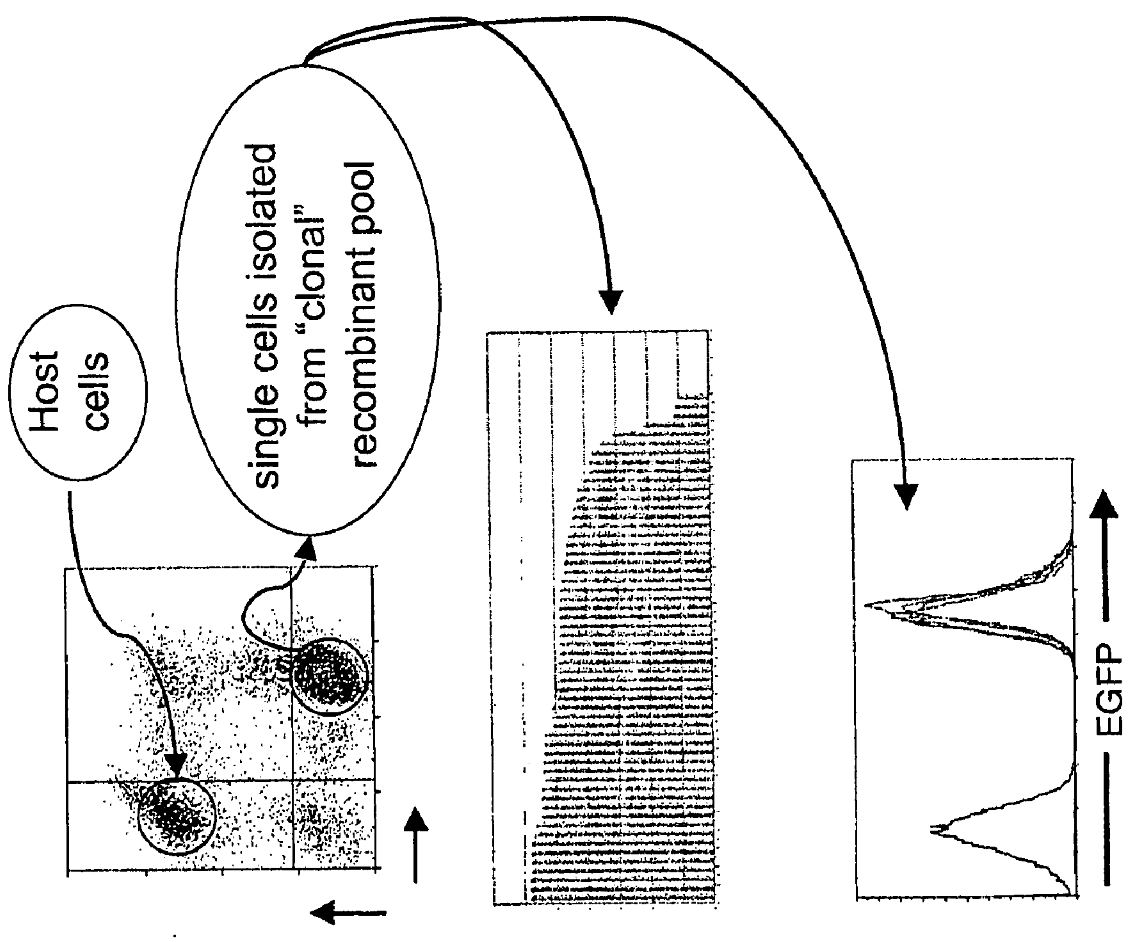
FIG. 7 illustrates clonal characteristics of cells with respect to EESYR functionality. For the top plot, major tick labels on both the y- and x-axes of the top plot represent $10^0$, $10^1$, $10^2$, $10^3$, and $10^4$; quadrant identifiers are R10 and R11 (top, left to right) and R12 and R13 (bottom, left to right). For the middle plot, which shows 96-well plate ELISA results of sorted single cells, the y-axis of the center plot represents Titer (μg/ml), with major tick labels of 0, 2, 4, 6, 8, 10, 12, and 14; whereas the x-axis represents Clone Number (in triplicate) from 1 to 63. For the bottom plot, which shows clone stability after three months without selection, y-axis major ticks represent increments of 100 from 0 to 1000. For the bottom plot, the left peak is for "Host," whereas the right peak is for "Recombinant clones."

EESYR recombinant cell pools display clonal characteristics. FIG. 7 illustrates clonal characteristics of EESYR recombinant pools. In the two-color FACS plot representing a dual parameter histogram of cells labeled with red or green markers (red cells are host CHO cells; green cells are recombinants expressing a GOI), EESYR recombinant pools show clustering in the plot that reflects substantially identical growth and expression, flow cytometry profile, and Southern analysis (not shown). A histogram of ELISAs of single cells demonstrate uniform expression in all clones. Clonal stability is also high after three months without selection.

Figure 8:
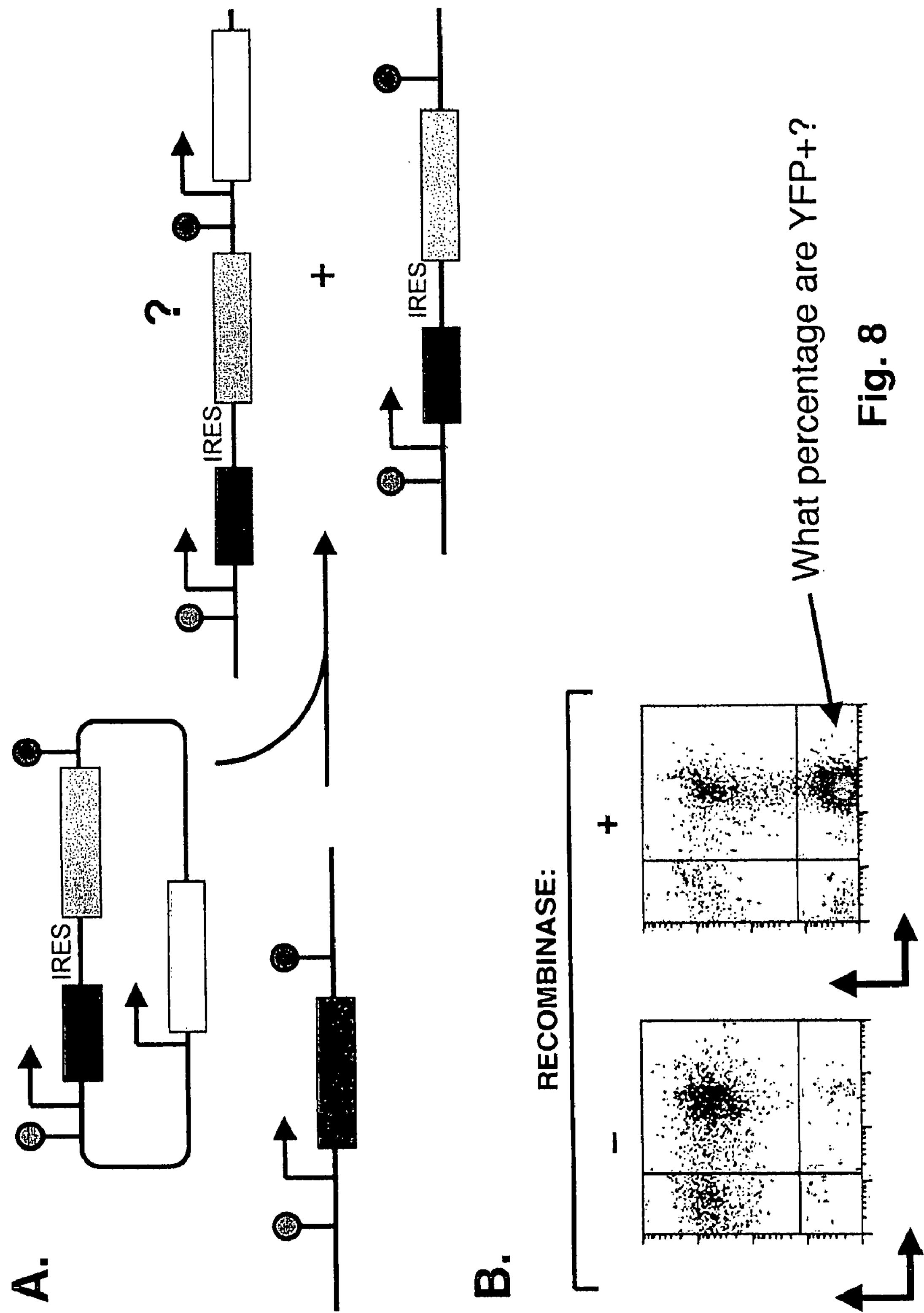
FIG. 8 illustrates that EESYR cells undergo specific and efficient recombination. In Panel B, y- and x-axes maior ticks represent $10^0$, $10^1$, $10^2$, $10^3$, and $10^4$ for each plot, quadrants are (left to right, top) R2 and R3, and (left to right, bottom) R4 and R5.

EESYR recombinants undergo specific and efficient recombination, as shown in FIG. 8. Panel A shows two markers separated by an IRES and flanked by recombinase recognition sites, and a third marker not flanked by recombinase recognition sites as a random integration control. When recombined at an EESYR locus comprising a marker flanked by two recombinase recognition sites, recombination is specific. Panel B shows little random integration in the absence of recombinase, but efficient and site-specific integration in the presence of recombinase.

Figure 9:
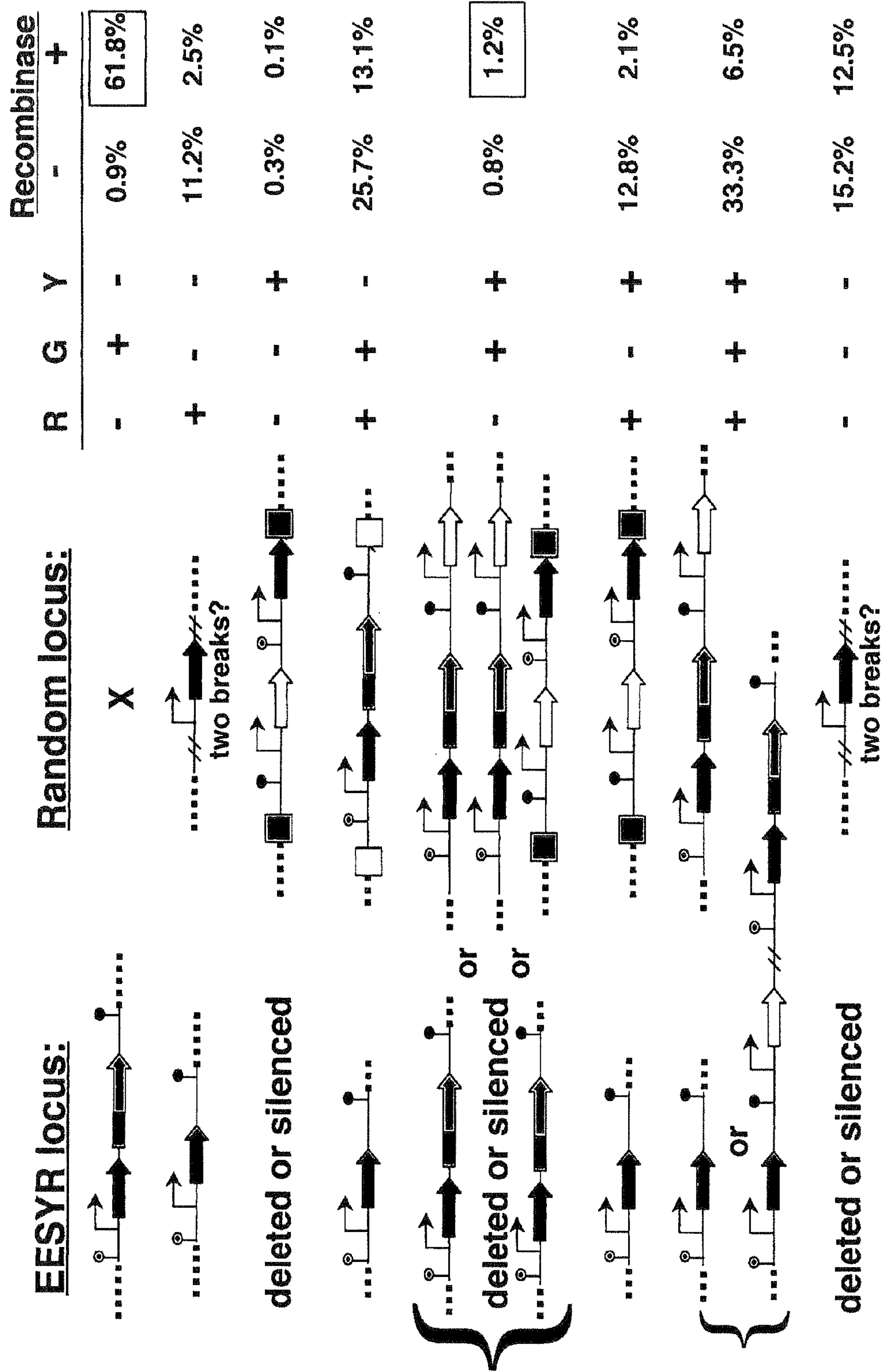
FIG. 9 illustrates the rarity of random integration events in EESYR cells.

Random integration using site specific recombination at an EESYR is rare (see FIG. 9). FIG. 9 shows that when random integration events are visualized, such events represent only a tiny fraction of integration events.

Figure 11:
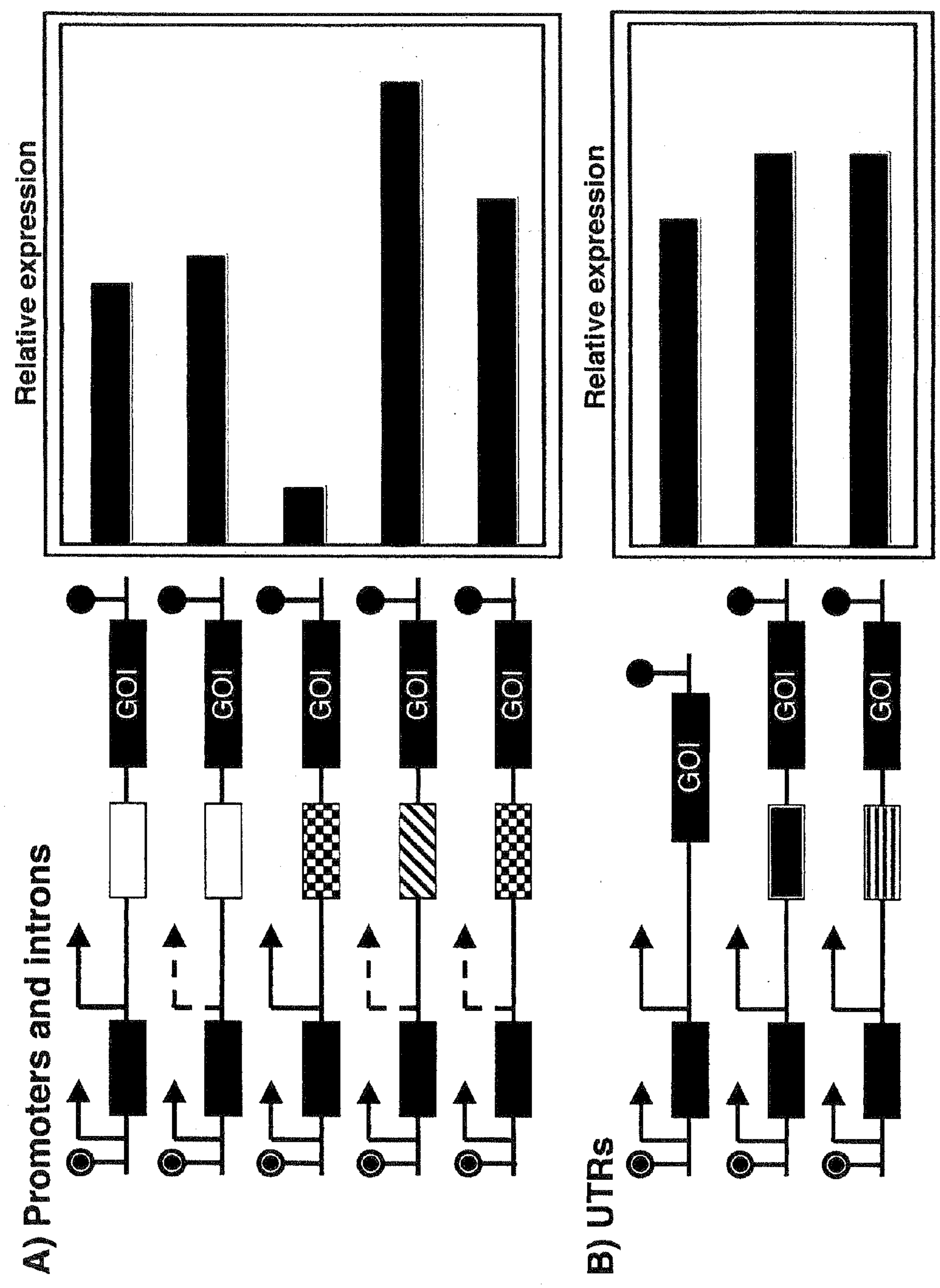
FIG. 11 illustrates testing promoters, introns, and UTRs using an EESYR system.

In another embodiment, EESYR cis-acting elements can be assessed using the methods and compositions of the invention. As shown in FIG. 10, EESYR recombinant cells, allows comparison of cis-acting elements equivalently. Because EESYR recombinants behave as a clonal population, differences in gene expression as the result of, for example, the presence or absence of suspected cis-acting elements, can be directly compared. Isogenic cell lines allow direct comparison of cis-acting elements. Using an EESYR system, cis-acting elements, such as, for example, promoters, introns, and UTRs, are preferably located between recombination sites. Expression optimization can also be achieved, including, for example, expression cassette orientation and codon optimization. By way of example, FIG. 11 shows cassettes flanked with recombination recognition sites that contain a promoter, a marker, various cis-elements (here, introns in panel A; UTRs in panel B), and a GOI were integrated at an EESYR (SEQ ID NO: 1 at the 5' end, SEQ ID NO:2 at the 3' end). Relative expression of the GOI is shown on the right.

FIG. 12 shows an example of how protein optimization can be achieved using the methods and compositions of the invention. FIG. 12 confirms that optional placement of a cDNA for a light chain antibody gene is 5' to the a cDNA for a heavy chain antibody gene.

Proteins of Interest

A nucleic acid sequence encoding a protein of interest can be conveniently integrated into a cell comprising an EESYR having a recombinase recognition site through, for example, a recombinase-mediated cassette exchange (RMCE) process. Any protein of interest suitable for expression in eukaryotic cells can be used. For example, the protein of interest can be an antibody or fragment thereof, a chimeric antibody or fragment thereof, an ScFv or fragment thereof, an Fc-tagged protein or fragment thereof, a growth factor or a fragment thereof, a cytokine or a fragment thereof, or an extracellular domain of a cell surface receptor or fragment thereof.

Nucleic Acid Constructs

Recombinant expression vectors can comprise synthetic or cDNA-derived DNA fragments encoding a protein, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation, as described in detail below. Mammalian expression vectors can also comprise nontranscribed elements such as an origin of replication, other 5' or 3' flanking nontranscribed sequences, and 5' or 3' nontranslated sequences such as splice donor and acceptor sites. A selectable marker gene to facilitate recognition of transfectants may also be incorporated.

Transcriptional and translational control sequences in expression vectors useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of a heterologous DNA sequence. Early and late promoters are particularly useful because both are obtained easily from the SV40 virus as a fragment that also comprises the SV40 viral origin of replication (Fiers et al., Nature 273:113, 1978). Smaller or larger SV40 fragments may also be used. Typically, the approximately 250 bp sequence extending from the Hind III site toward the BglI site located in the SV40 origin of replication is included.

Bicistronic expression vectors used for the expression of multiple transcripts have been described previously (Kim S. K. and Wold B. J., Cell 42:129, 1985; Kaufman et al. 1991, supra) and can be used in combination with an EESYR sequence of the invention. Other types of expression vectors will also be useful, for example, those described in U.S. Pat. No. 4,634,665 (Axel et al.) and U.S. Pat. No. 4,656,134 (Ringold et al.).

Host Cells and Transfection

The eukaryotic host cells used in the methods of the invention are mammalian host cells, including, for example, CHO cells and mouse cells. In a preferred embodiment, the invention provides a nucleic acid sequence that encodes an EESYR sequence from a CHO cell. An integration site, for example, a recombinase recognition site, can be placed within an EESYR, or 5' or 3' to the EESYR sequence. One example of a suitable integration site is a lox p site. Another example of a suitable integration site is two recombinase recognition sites, for example, a lox p site and a lox 511 site. In one embodiment, the EESYR sequence is located on chromosome 6 of a CHO cell genome. In specific embodiments, the EESYR sequence is located within a sequence selected from the group consisting of nucleic acids comprising nucleotides 1-6473 and 4607-6473 of SEQ ID NO: 1; and 1-7045, 1-3115, 1-2245, 1-935, and 1-465 of SEQ ID NO:2.

The invention includes a mammalian host cell transfected with an expression vector of the invention. While any mammalian cell may be used, the host cell is preferably a CHO cell.

Transfected host cells include cells that have been transfected with expression vectors that comprise a sequence encoding a protein or polypeptide. Expressed proteins will preferably be secreted into the culture medium, depending on the nucleic acid sequence selected, but may be retained in the cell or deposited in the cell membrane. Various mammalian cell culture systems can be employed to express recombinant proteins. Examples of suitable mammalian host cell lines include the COS-7 lines of monkey kidney cells, described by Gluzman (1981) Cell 23:175, and other cell lines capable of expressing an appropriate vector including, for example, CV-1/EBNA (ATCC CRL 10478), L cells, C127, 3T3, CHO, HeLa and BHK cell lines. Other cell lines developed for specific selection or amplification schemes will also be useful with the methods and compositions provided herein. A preferred cell line is the CHO cell line designated K1. In order to achieve the goal of high volume production of recombinant proteins, the host cell line should be pre-adapted to bioreactor medium in the appropriate case.

Several transfection protocols are known in the art, and are reviewed in Kaufman (1988)

Meth. Enzymology 185:537. The transfection protocol chosen will depend on the host cell type and the nature of the GOI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner.

One commonly used method of introducing heterologous DNA into a cell is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., (1980) Proc. Natl. Acad. Sci. USA 77:2163) is another useful method of introducing heterologous DNA. Protoplast fusion protocols frequently yield multiple copies of the plasmid DNA integrated into the mammalian host cell genome, and this technique requires the selection and amplification marker to be on the same plasmid as the GOI.

Electroporation can also be used to introduce DNA directly into the cytoplasm of a host cell, for example, as described by Potter et al. (Proc. Natl. Acad. Sci. USA 81:7161, 1988) or Shigekawa et al. (BioTechniques 6:742, 1988). Unlike protoplast fusion, electroporation does not require the selection marker and the GOI to be on the same plasmid.

More recently, several reagents useful for introducing heterologous DNA into a mammalian cell have been described. These include Lipofectin™ Reagent and Lipofectamine™Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method for amplifying the GOI is also desirable for expression of the recombinant protein, and typically involves the use of a selection marker (reviewed in Kaufman supra). Resistance to cytotoxic drugs is the characteristic most frequently used as a selection marker, and can be the result of either a dominant trait (e.g., can be used independent of host cell type) or a recessive trait (e.g., useful in particular host cell types that are deficient in whatever activity is being selected for). Several amplifiable markers are suitable for use in the expression vectors of the invention (e.g., as described in Maniatis, Molecular Biology: A Laboratory Manual, Cold Spring Harbor Laboratory, NY, 1989; pgs 16.9-16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Maniatis supra, pgs 16.9-16.15). Co-transfection protocols employing two dominant selectable markers have also been described (Okayama and Berg, Mol. Cell Biol 5:1136, 1985).

Useful regulatory elements, described previously or known in the art, can also be included in the nucleic acid constructs used to transfect mammalian cells. The transfection protocol chosen and the elements selected for use therein will depend on the type of host cell used. Those of skill in the art are aware of numerous different protocols and host cells, and can select an appropriate system for expression of a desired protein, based on the requirements of the cell culture system used.

Other features of the invention will become apparent in the course of the following descriptions of exemplary embodiments which are given for illustration of the invention and are not intended to be limiting thereof.

EXAMPLES

The following examples are put forth so as to provide those of ordinary skill in the art how to make and use the methods and compositions described herein, and are not intended to limit the scope of what the inventors regard as their invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1

Generation of RGC9 and RGC16 Cell Lines

CHO K1 cells ($1\times10^7$) were infected with pantropic retrovirus produced with plasmid pTE252 (FIG. 1), having a lox p site in it, at an MOI of less than 1 to generate a stable pool of cells with mostly one retroviral insertion per cell. Cells in the stable pool that expressed a marker protein at a high level were selected and expanded. Selection rounds were conducted to identify cell populations capable of enhanced expression. Thirty-six clones were isolated and expanded into 36 cell lines. Clones exhibiting the highest recombination efficiency were identified and cloned, wherein the clones each contained at least one recombinase recognition site in an enhanced expression locus. Eight cell populations with the best recombination efficiency were selected, and reassessed for enhanced protein expression. Two cell populations were selected and designated RGC9 and RGC16. Southern blot analysis of the cell populations from the original 36 cell lines that corresponded to these two cell lines showed that a single copy of a reporter construct was integrated into the CHO cell genome at the same locus in the case of both cell populations, and the location of integration was determined to be at the triplet “act” at nucleotide position 6,471 to 6,473 of SEQ ID NO:5. At least one of these two cell lines were employed in experiments described below.

Example 2

Expression of FcFP1 Protein in Serum-Free Production Medium

RGC38 cells were derived from RGC9 cells and were adapted to grow in suspension in a serum-free production medium. RGC38 cells were used as host cells for the expression of FcFP1 protein (Fc fusion protein-1). RGC38 cells were transfected in a ten-centimeter plate with a FcFP1 expression vector, pTE851 and a Cre plasmid, pRG858. The FcFP1 plasmid has, in 5' to 3' direction, a LoxP site, a SV40 late promoter, a hygromycin resistant gene, an IRES, an eGFP, a CMV MIE promoter, a gene encoding a FcFP1 protein, and a Lox511 site. Cells were cultured in F12 medium with 400 μg/ml hygromycin for two weeks after transfection. Cells expressing eGFP but not DsRed were isolated using flow cytometry and designated as RS421-1. Isolated cells were essentially isogenic, though derived from different founder cells. RS421-1 cells were expanded in suspension cultures in serum-free production medium. FcP1 protein in conditioned medium of 3-day old cultures was examined in SDS-PAGE with Coomassie blue staining. FcF1 protein in the conditioned medium was abundant and could be seen without purification.

Example 3

Regulated Expression of FcFP1 Protein in Serum-free Production Medium

RGC49 cells were derived from RGC16, were adapted to grow in serum-free production medium, and contained a stably integrated tetR-YFP expression plasmid, pcDNA6/TR. The tetR protein allows regulation of transcription from promoters that comprise a tet operator sequence by tetracycline or doxycycline. RGC49 cells were co-transfected with pTE851 and pRG858. The transfected cells were selected with 400 μg/ml hygromycin for two weeks. Cells expressing eGFP but not YFP were isolated using flow cytometry and designated as RS569-1. RS569-1 cells were expanded in suspension cultures in serum-free production medium in the presence or absence of doxycycline. FcP1 protein in conditioned medium of 3-day old cultures was examined by SDS-PAGE and Coomassie blue staining. The RS569-1 cells expressed FcFP1 protein similarly to RS421-1 upon in the presence of 1 μg/ml doxycycline in the culture medium. Very little FcFP1 protein was detected from the RS569-1 cells in the absence of doxycycline.

Example 4

Dual Lox Cell Line Construction

RGC23 cells were derived from RGC16, were adapted to grow in Sigma CHO SSM serum-free medium (Saint Louis, Mo.), and carried DsRed. RGC23 cells were transfected with a Cre plasmid, pRG858 and a eGFP and FcFP2 protein expression vector, pTE357. The FcFP2 vector has, in 5' to 3' direction, a LoxP site, a SV40 late promoter, a hygromycin resistant gene, a CMV MIE promoter, a gene encoding FcFP2 protein, an IRES, an eGFP, and a Lox511 site. Cells expressing both DsRed and eGFP were collected and a single cell was isolated. The isolated cell was expanded in culture, and the resulting cell line was designated RS398-2-6. RS398-2-6 was then transfected with pRG858 (Cre plasmid) and pRG1231, a eCFP expression plasmid. pRG1231 has, in 5' to 3' direction, a LoxP site, a CMV MIE promoter, a puromycin resistant gene, an IRES, an eCFP, and a Lox511 site. Cells expressing DsRed and eCFP but not eGFP were isolated by flow cytometry as a pool and designated as RS630.

Example 5

Antibody Heavy Chain and Light Chain Expression Using a Dual Lox Cell Line

RS630 cells were transfected with pTE828, a 15G1 antibody heavy chain and eGFP expression vector, pTE829, a 15G1 antibody light chain and eYFP expression vector, and pRG858. pTE828 has, in 5' to 3' direction, a LoxP site, a SV40 late promoter, a hygromycin resistant gene, an IRES, an eGFP, a CMV MIE promoter, the heavy chain gene of 15G1 antibody, and a Lox511 site. pTE829 has, in 5' to 3' direction, a LoxP site, a SV40 late promoter, a neomycin resistant gene, an IRES, an eYFP, a CMV MIE promoter, the light chain gene of 15G1 antibody, and a Lox511 site. The transfected cultures were selected with hygromycin and G418 at 400 μg/ml each for two weeks. Cells expressed both YFP and eGFP but neither dsRed nor eCFP were isolated by flow cytometry. The isolated cells were expanded in suspension culture in serum-free production medium and were designated as RS631 cells. Aliquots of conditioned medium from 3-day old culture were analyzed by SDS-PAGE. The antibody products from RS631 cells were readily detected by Coomassie blue staining.

Example 6

Use of a Third Lox Site (Lox2272) at EESYR to Create Dual Expression Cassette

Cells from any cell line carrying a DsRED gene flanked by a LoxP site and a Lox511 site at EESYR locus are transfected with pRG858 and a vector comprising, in 5' to 3' direction, a LoxP site, a first promoter, a YFP, a Lox2272 site, a second promoter, an eGFP, and a Lox511. Cells expressing eGFP and YFP, but not DsRed are isolated. Isolated cells are then transfected with pRG858, pRG1167 (a vector that has, in 5' to 3' direction, a LoxP site, a SV40 late promoter, a hygromycin resistant gene, a CMV MIE promoter, a DsRed and a Lox2272 site) or pRG1234 (a vector that has, in 5' to 3' direction, a Lox2272 site, a SV40 late promoter, a hygromycin resistant gene, a CMV MIE promoter, a DsRed and a Lox511 site). Cells capable of expressing either DsRED and eGFP but not YFP, or DsRED and YFP but not eGFP, are isolated.

Example 7

Antibody Expression from RGC38 Host Cells

RGC38 cells were transfected with pTE963 and pRG858. pTE963 has, in 5' to 3' direction, a LoxP site, a SV40 late promoter, a hygromycin resistant gene, an IRES, an eGFP, a CMV MIE promoter, the light chain gene of 15G1 antibody, a CMV MIE promoter, the heavy chain gene of 15G1 antibody, and a Lox511 site. The transfected cultures were selected with hygromycin at 400 μg/ml each for two weeks. Cells that expressed eGFP but not dsRed were isolated by flow cytometry. The isolated cells were expanded in suspension in serum-free production medium and were named as RS533 cells. For the production of 15G1 antibodies, RS533 cells were cultured in a bioreactor for 10 days. Aliquots of spent medium from day six to day ten were collected and their protein composition was analyzed by SDS-PAGE. The heavy chain and light chain peptide of the 15G1 antibody in the reactor spent medium were readily detected by Coomassie blue staining.

Example 8

Rescuing and Subcloning EESYR Sequences

A CHO cell line (designated RGC21) expressing high levels of a reporter gene, DsRed, was selected for isolation of EESYR sequences, since Southern blot analysis indicated that the high expression of DsRed expression observed for this cell line is driven by a single integration of an expression cassette encoding DsRed. Genomic sequences 5' to the expression cassette were rescued by transfecting RGC21 cells with linearized pTE494 plasmids, a vector that has, in 5' to 3' direction, a LoxP site, an ampicillin resistance gene, a bacterial origin of replication, a CMV MIE promoter, a neomycin phosphotransferase gene, an IRES, an eGFP and a Lox511 site. Cells expressing eGFP but not DsRed were isolated by flow cytometry as a pool. Genomic DNA was isolated, digested with Xbal restriction endonuclease, and self ligated to create pRG1106. Genomic sequences 3' to the expression cassette were rescued by transfecting RGC21 cells with circular pTE495 plasmids, a vector that has, in 5' to 3' direction, a LoxP site, a CMV MIE promoter, a neomycin phosphotransferase gene, an IRES, an eGFP, a bacterial origin of replication, an ampicillin resistance gene, and a Lox511 site. Cells expressing eGFP but not DsRed were isolated by flow cytometry as a pool. Genomic DNA was isolated, digested with Mfel restriction endonuclease, and self ligated to create pRG1099.

Example 9

Plasmid Construction for EESYR Analysis

EESYR sequences were excised from either pRG1106 or pRG1099 as Agel fragments and inserted into the Agel and NgoMIV sites of pTE575, a plasmid expressing FCFP2, to yield plasmid pTE809. The pTE575 plasmid has, in 5' to 3' direction, a SV40 late promoter, a hygromycin resistant gene, a CMV MIE promoter, and a gene encoding FCFP2 protein. In stably transfected CHO cells, pTE809 and pTE575 yielded 97.22% and 38.57% of cells expressing detectable levels of FCFP2 protein, respectively. The mean fluorescence of FcFP2 detected by an FITC conjugated antibody was 482.54 and 279.75 for cultures transfected with pTE809 and pTE575, respectively. Thus, the inclusion of EESYR in expression vectors increased the expression of FCFP2 protein in stable transfection.

The present invention may be embodied in other specific embodiments without departing from the spirit or essence thereof.

We claim:

1. An isolated cell comprising an expression-enhancing sequence selected from SEQ ID NO:1-6, and at least one recombinase recognition site located immediately adjacent to SEQ ID NO:1-6.

2. The isolated cell of claim 1, wherein the at least one recombinase recognition site is selected from the group consisting of a loxp site, a lox 511 site, a lox 2272 site, and a frt site.

3. The isolated cell of claim 1, further comprising a first gene of interest (GOI) encoding a protein, wherein the first GOI is integrated at the at least one recombinase recognition site.

4. The isolated cell of claim 3, wherein the GOI is operably linked to a promoter.

5. The isolated cell of claim 3, wherein the GOI encodes a protein selected from an antibody light chain or antigen-specific fragment thereof, an antibody heavy chain or antigen-specific fragment thereof, an Fc fusion protein, a ligand, and a receptor or ligand-specific fragment thereof.

6. The isolated cell of claim 3, further comprising a second GOI encoding a protein, wherein a recombinase recognition site is present between the first GOI and the second GOI.

7. The isolated cell of claim 6, further comprising a recombinase recognition site 5' to the first GOI and a recombinase recognition site 3' with respect to the second GOI.

8. The isolated cell of claim 7, wherein the first GOI and the second GOI are independently selected from the group consisting of a gene encoding for an antibody light chain or antigen-specific fragment thereof, an antibody heavy chain or antigen-specific fragment thereof, an Fc fusion protein, and a receptor or ligand-specific fragment thereof.

* * * * *